(12) United States Patent
Jahns et al.

(10) Patent No.: US 8,454,634 B2
(45) Date of Patent: Jun. 4, 2013

(54) VESSEL SEALING DEVICES

(75) Inventors: Scott E. Jahns, Hudson, WI (US);
James R. Keogh, Mpalewood, MN
(US); Paul A. Pignato, Stacy, MN (US);
Christopher P. Olig, Eden Prairie, MN
(US); Karen P. Montpetit, Mendota
Heights, MN (US); Cynthia T. Clague,
Minnetonka, MN (US); **Raymond W.
Usher, Coon Rapids, MN (US); Philip J.
Haarstad, Chanhassen, MN (US); Gary
W. Guenst**, Collegeville, PA (US)

(73) Assignee: Medtronic, Inc., Minneapolis, MN (US)

( * ) Notice: Subject to any disclaimer, the term of this patent is extended or adjusted under 35 U.S.C. 154(b) by 154 days.

(21) Appl. No.: 11/604,956

(22) Filed: Nov. 28, 2006

(65) Prior Publication Data

US 2007/0073344 A1 Mar. 29, 2007

Related U.S. Application Data

(62) Division of application No. 10/763,861, filed on Jan. 22, 2004, now abandoned.

(51) Int. Cl.
*A61B 17/08* (2006.01)
*A61D 1/00* (2006.01)

(52) U.S. Cl.
USPC .......................................... 606/153; 606/213

(58) Field of Classification Search
USPC .................. 606/153, 213, 215, 151, 154–156, 606/191
See application file for complete search history.

(56) References Cited

U.S. PATENT DOCUMENTS

| | | | |
|---|---|---|---|
| 3,480,017 A | 11/1969 | Shute |
| 4,137,922 A | 2/1979 | Leininger et al. |
| 4,682,606 A | 7/1987 | DeCaprio |
| 5,258,000 A | 11/1993 | Gianturco |
| 5,366,478 A | 11/1994 | Brinkerhoff et al. |
| 5,383,856 A | 1/1995 | Bersin |
| 5,383,896 A | 1/1995 | Gershony et al. |
| 5,385,606 A | 1/1995 | Kowanko |
| 5,452,733 A | 9/1995 | Sterman et al. |
| 5,464,447 A | 11/1995 | Fogarty et al. |
| 5,690,674 A | 11/1997 | Diaz |
| 5,695,504 A | 12/1997 | Gifford et al. |
| 5,702,412 A | 12/1997 | Popov et al. |
| 5,707,380 A | 1/1998 | Hinchliffe et al. |
| 5,716,392 A | 2/1998 | Bourgeois et al. |
| 5,725,544 A | 3/1998 | Rygaard |
| 5,766,151 A | 6/1998 | Valley et al. |
| 5,776,154 A | 7/1998 | Taylor et al. |
| 5,799,661 A | 9/1998 | Boyd et al. |
| 5,865,754 A | 2/1999 | Sevick-Muraca et al. |
| 5,868,770 A | 2/1999 | Rygaard |
| 5,875,782 A | 3/1999 | Ferrari et al. |

(Continued)

FOREIGN PATENT DOCUMENTS

EP 0 895 753 2/1999

*Primary Examiner* — Gary Jackson
*Assistant Examiner* — Lindsey Bachman

(57) ABSTRACT

A device for temporarily sealing an opening in a blood vessel is provided. The device comprises a cutting mechanism for creating an opening in a blood vessel and a seal for sealing the opening in the blood vessel. The seal is delivered through an inner lumen of a tool body coupled to the cutting mechanism. Methods for using the device to construct an anastomosis between two vessels are also provided.

10 Claims, 34 Drawing Sheets

U.S. PATENT DOCUMENTS

| | | |
|---|---|---|
| 5,893,369 A | 4/1999 | LeMole |
| 5,944,730 A | 8/1999 | Nobles et al. |
| 5,947,991 A | 9/1999 | Cowan |
| 5,972,017 A | 10/1999 | Berg et al. |
| 5,976,069 A | 11/1999 | Navia et al. |
| 5,976,178 A | 11/1999 | Goldsteen et al. |
| 6,026,814 A | 2/2000 | LaFontaine et al. |
| 6,068,608 A | 5/2000 | Davis et al. |
| 6,068,637 A | 5/2000 | Popov et al. |
| 6,071,295 A | 6/2000 | Takahashi |
| 6,080,175 A | 6/2000 | Hogendijk |
| 6,120,436 A | 9/2000 | Anderson et al. |
| 6,132,397 A | 10/2000 | Davis et al. |
| 6,165,196 A | 12/2000 | Stack et al. |
| 6,171,319 B1 | 1/2001 | Nobles et al. |
| 6,180,848 B1 | 1/2001 | Flament et al. |
| 6,193,734 B1 | 2/2001 | Bolduc et al. |
| 6,231,565 B1 | 5/2001 | Tovey et al. |
| 6,234,995 B1 | 5/2001 | Peacock |
| 6,248,117 B1 | 6/2001 | Blatter |
| 6,254,570 B1 | 7/2001 | Rutner et al. |
| 6,299,598 B1 | 10/2001 | Bander |
| 6,331,158 B1 | 12/2001 | Hu et al. |
| 6,332,468 B1 | 12/2001 | Benetti |
| 6,371,964 B1 | 4/2002 | Vargas et al. |
| 6,395,015 B1 * | 5/2002 | Borst et al. .................... 606/213 |
| 6,398,797 B2 * | 6/2002 | Bombard et al. ............. 606/153 |
| 6,428,551 B1 | 8/2002 | Hall et al. |
| 6,428,555 B1 | 8/2002 | Koster, Jr. |
| 6,496,267 B1 | 12/2002 | Takaoka |
| 6,689,071 B2 | 2/2004 | Burbank et al. |
| 6,786,915 B2 | 9/2004 | Akerfeldt et al. |
| 6,916,331 B2 | 7/2005 | Mollenauer et al. |
| 7,128,073 B1 | 10/2006 | van der Burg et al. |
| 7,182,769 B2 | 2/2007 | Ainsworth et al. |
| 7,195,636 B2 | 3/2007 | Avellanet et al. |
| 2002/0077637 A1 | 6/2002 | Vargas et al. |
| 2002/0169362 A1 | 11/2002 | Kan et al. |
| 2004/0102797 A1 * | 5/2004 | Golden et al. ................ 606/153 |
| 2004/0215231 A1 | 10/2004 | Fortune et al. |
| 2005/0165427 A1 | 7/2005 | Jahns et al. |
| 2007/0073343 A1 | 3/2007 | Jahns et al. |
| 2010/0174281 A1 | 7/2010 | Jahns et al. |

* cited by examiner

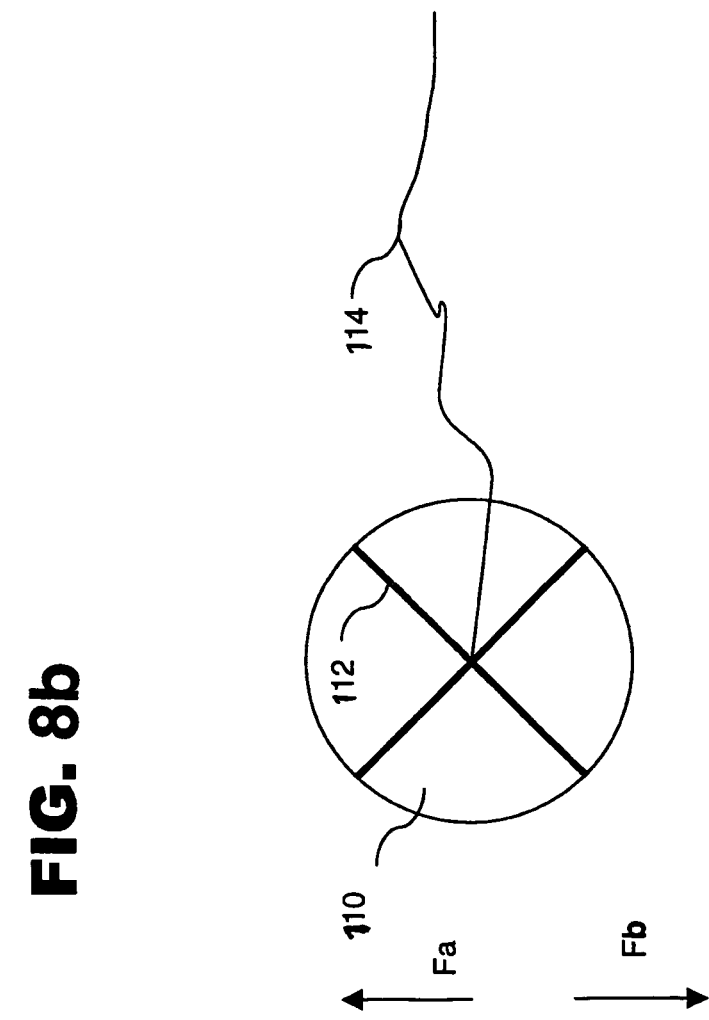
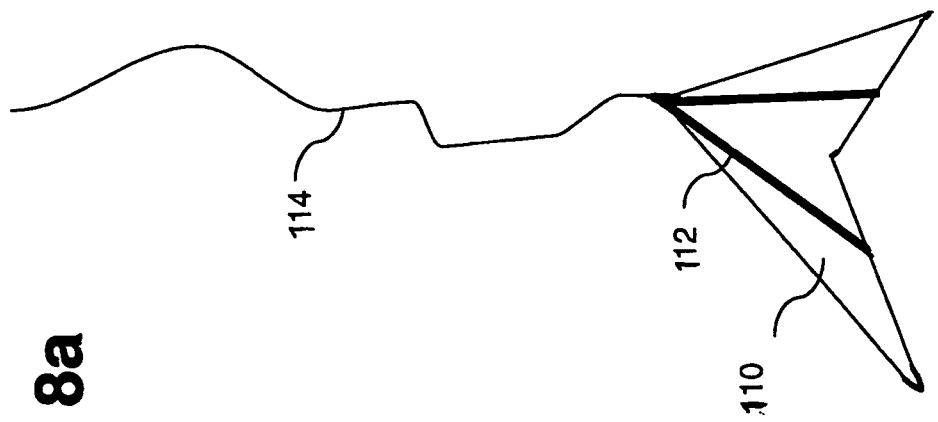
FIG. 8b
FIG. 8a

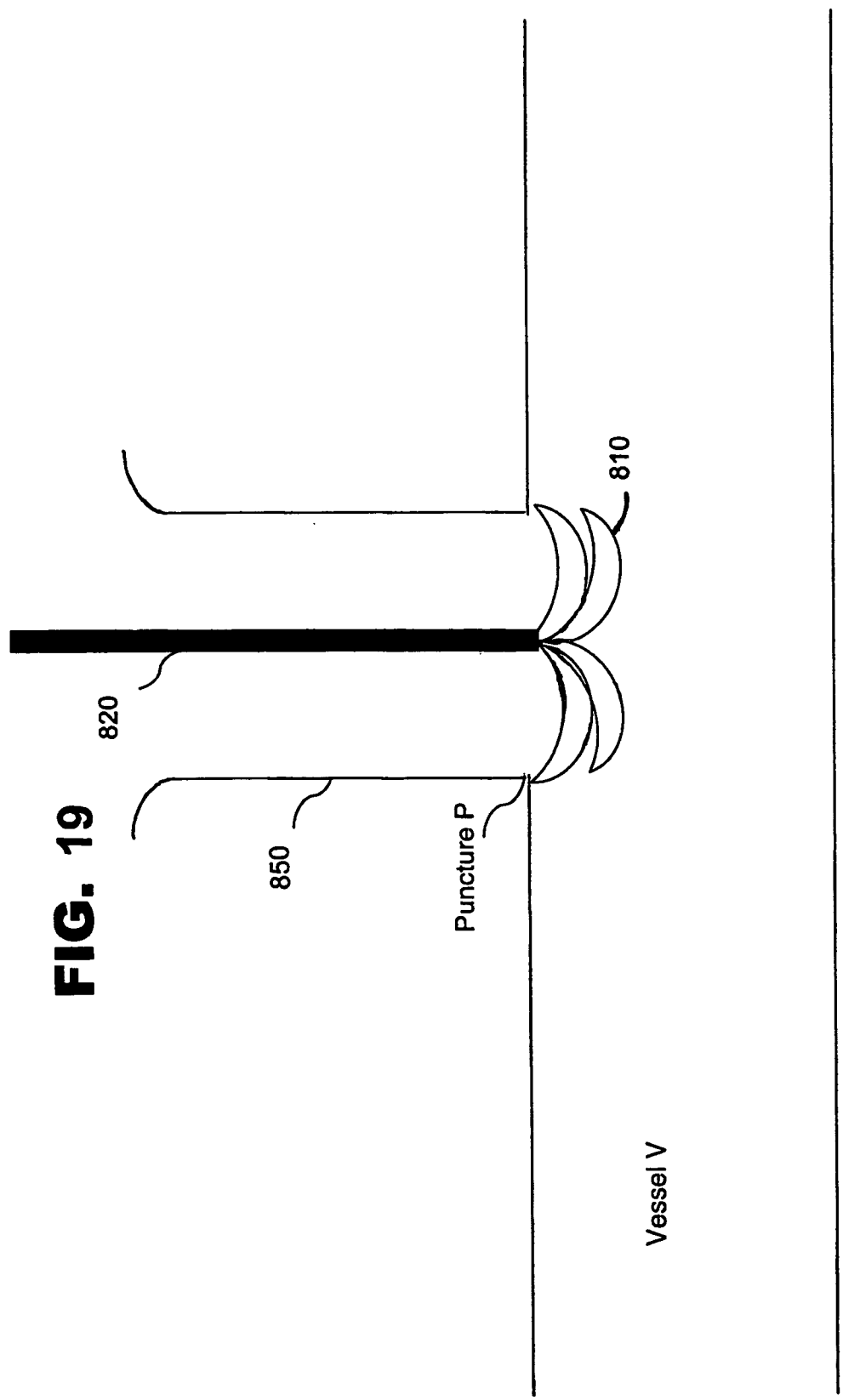

VESSEL SEALING DEVICES

CROSS REFERENCE TO RELATED APPLICATION

This application is a divisional of U.S. patent application Ser. No. 10/763,861, filed, Jan. 22, 2004 now abandoned.

FIELD OF THE INVENTION

The present invention relates to the field of medical methods and devices for occluding and/or sealing incisions in vessels of the body. More particularly, the invention relates to devices that are capable of creating and sealing incisions in cardiac blood vessels in order to facilitate a medical procedure, such as an anastomosis, on a stopped or beating heart.

BACKGROUND OF THE INVENTION

The current leading cause of death in the United States is coronary artery disease (CAD) which is the occlusion or blockage of the coronary arteries by atherosclerotic plaques or fatty deposits. Occlusions in the coronary arteries generally causes chest pain (angina) and/or heart attacks (myocardial infarction) due to a lack of blood flow, i.e. oxygen, to the tissues of the heart. The lack of oxygen in tissues of the heart causes myocardial ischemia. Severe and prolonged myocardial ischemia can produce cardiac dysfunction, heart muscle damage and possibly death.

One treatment to relieve a partially or fully blocked coronary artery is coronary artery bypass graft (CABG) surgery. CABG surgery, also known as "heart bypass" surgery, generally entails the use of a graft or conduit to bypass the coronary obstruction and, thereby provide blood flow to the downstream ischemic heart tissues. More particularly, a fluid connection or "anastomosis" is surgically established between a source vessel of oxygenated blood and the obstructed or restricted target coronary artery downstream or distal to the obstruction or restriction to restore the flow of oxygenated blood to the heart muscle. In one approach, the surgeon attaches an available source vessel, e.g., an internal mammary artery (IMA), directly to the obstructed target coronary artery at the distal anastomosis site downstream from the obstruction or restriction.

Conventional CABG procedures are typically conducted on a cardioplegic arrested heart while the patient is on cardiopulmonary bypass (CPB). A stopped heart and a CPB circuit enable a surgeon to work in a relatively motionless, bloodless operative field, however there are a number of problems associated with CABG procedures performed while on CPB. For example, problems associated with conventional CABG procedures may include the initiation of a systemic inflammatory response due to the interactions of blood elements with the artificial material surfaces of the CPB circuit, global myocardial ischemia due to global (hypothermic) cardiac arrest, and post-operative stroke due to clamping of the aorta. In addition, the use of a partial side-biting aortic clamp used to isolate a portion of the aorta can also cause trauma to the patient. The use of clamps can add to the time required for performing the procedure, as well as the use of clamps may dislodge plaques from the vessel being clamped resulting, for example, in neurologic injury. The clamping pressure can also cause damage to the endothelial lining of the aorta. Post-operative scarring can provide an irregular surface causing increased plaque build up.

Obstructed coronary arteries are generally bypassed; for example, with an in situ internal mammary artery (IMA) or a reversed segment of saphenous vein harvested from a leg. Segments of other suitable blood vessels may also be used for grafting depending on availability, size and quality. In general, the body hosts seven potential arterial conduits, the right and left IMAs, the radial arteries and three viceral arteries, one in the abdomen, and two in the lower abdominal wall, though the latter may be quite short and are generally of limited usefulness. The viceral arteries include the gastroepiploic artery and the splenic artery.

The left IMA is best used for bypass to the left anterior descending (LAD) coronary artery and its diagonal branches. Whereas, the right IMA may be used for bypass to selected vessels more posterior such as the distal right coronary artery (RCA). The right IMA may also be used for bypass to selected marginal branches of the left circumflex coronary artery. A segment of radial artery harvested from an arm is generally used to revascularize the posterior surface of the heart. The right gastroepiploic artery may be used to revascularize almost any artery on the surface of the heart. It is most commonly used for bypass to the distal RCA or the posterior descending coronary artery. In unusual circumstances the splenic artery is used to revascularize posterior coronary arteries, but it is long enough to reach the marginal branches of the circumflex coronary artery.

Surgeons generally complete bypass grafts to the following coronary arteries in a patient undergoing multiple bypass surgery in roughly the following order: posterior descending coronary artery (PDA), RCA, obtuse marginal branch, circumflex coronary artery, diagonal branch, and LAD. More generally, surgeons will revascularize the three coronary systems in the following order: right, circumflex, and anterior descending. However, the order may vary depending on whether the procedure is performed on a beating heart or an arrested heart. For arrested heart, about 3 to 4 bypass grafts of which 1 to 3 are free grafts are generally performed per procedure. In contrast, about 2 to 3 bypass grafts of which 0 to 2 are free grafts are generally performed per beating heart procedure. In general, 1 free graft is used per beating heart procedure.

When a saphenous vein or other blood vessel is used as a free graft in a procedure, two anastomoses are performed; one to the diseased artery distal to the obstruction (outflow end), and one proximally to the blood vessel supplying the arterial blood (inflow end). These anastomoses are generally performed using end-to-side and/or side-to-side anastomotic techniques. Rarely an end-to-end anastomotic technique is used. When more than one graft is required in any of the three coronary systems for complete revascularization of the heart, sequential graft techniques may be used to conserve the amount of blood vessels required. Sequential graft techniques use proximal side-to-side anastomoses and an end-to-side anastomosis to complete the graft. For example, a common sequence used in the anterior descending coronary system is a side-to-side anastomosis of graft to the diagonal branch and an end-to-side anastomosis of graft to the LAD coronary artery.

The majority of surgeons will complete the distal anastomosis of a graft prior to completion of the proximal anastomosis. The small percentage of surgeons who do complete the proximal anastomosis first usually do so to allow antegrade perfusion of cardioplegic solution through the graft during revascularization. Construction of the distal anastomosis, e.g., a saphenous vein-coronary artery anastomosis, begins by first locating the target artery on the heart. Next, an incision is made through the epicardium and the myocardium to expose the artery. An arteriotomy is then made using a knife to incise the artery. The incision is then extended with a scissors. The length of the incision approximates the diameter of the saphenous vein, about 4 to 5 mm. The diameter of the target artery is generally 1.5 to 2.0 mm. Since, most surgeons feel the distal take-off angle should be 30 to 45 degrees, the distal end of the saphenous vein is beveled at about 30 to 45 degrees.

Most surgeons construct the anastomosis via a ten-stitch running suture using 7-0 polypropylene suture material. The ten-stitch anastomosis typically comprises five stitches around the heel of the graft and five stitches around the toe. The five stitches around the heel of the graft comprise two stitches to one side of the apex of the graft and the artery, a stitch through the apex and two stitches placed at the opposite side of the apex. The graft is generally held apart from the coronary artery while the stitches are constructed using a needle manipulated by a forceps. Suture loops are drawn up and the suture pulled straight through to eliminate purse-string effect. The five stitches around the toe of the graft also comprises two stitches to one side of the apex of the graft and the artery, a stitch through the apex and two stitches placed at the opposite side of the apex. Again, suture loops are drawn up and the suture pulled straight through to eliminate purse-string effect. The suture ends are then tied.

The proximal anastomosis of a saphenous vein graft to the aorta, i.e., an aortosaphenous vein anastomosis, is generally formed by first removing the pericardial layer that covers the aorta. An occluding or side-biting clamp may be placed on the aorta at the anastomosis site. A small circular or elliptical portion of the ascending aorta is excised forming a small opening 4 to 5 mm in diameter. An aortic punch typically facilitates this procedure. The opening for a right-sided graft is made anterior or to the right lateral side of the aorta, whereas an opening for a left-sided graft is made to the left lateral side of the aorta. If the graft is to supply blood to the right coronary artery, the opening is made proximal on the aorta. If the graft is to supply blood to the anterior descending coronary artery, the opening is made in the middle on the aorta. And, if the graft is to supply blood to the circumflex artery, the opening is made distal on the aorta. The right graft opening is placed slightly in the right of the anterior midpoint of the aorta and the left graft opening slightly to the left. The end of the saphenous vein is cut back longitudinally for a distance of approximately 1 cm. A vascular clamp is placed across the tip of the saphenous vein to flatten it, thereby exposing the apex of the vein. Five suture loops of a running suture using 5-0 polypropylene are then placed around the 'heel' of the graft and passed through the aortic wall. Two stitches are placed on one side of the apex, the third stitch is placed precisely through the apex of the incision in the saphenous vein, and the final two stitches are placed on the opposite side of the apex. Suture traction is used to help expose the edge of the aortic opening to ensure accurate needle placement. Stitches include about 3 to 5 mm of the aortic wall for adequate strength. Suture loops are then pulled up to approximate the vein graft to the aorta. The remaining stitches are placed in a cartwheel fashion around the aortic opening thereby completing the remainder of the anastomosis.

Left-sided grafts are oriented so the apex of the incision in the "heel" of the saphenous vein will face directly to the left side. The stitches are placed in a clockwise fashion around the heel of the graft and in a counterclockwise fashion around the aortic opening. Right-sided grafts are oriented in a caudal fashion. The stitches are placed in a counterclockwise fashion around the heel of the graft and in a clockwise fashion around the aortic opening. Five suture loops complete the heel portion of the graft and an additional five or six are necessary to complete the toe of the graft. Finished proximal anastomoses usually have a "cobra-head" appearance.

It is essential for the surgeon to take steps to minimize the possibility of thrombosis, narrowing and/or premature closure of the anastomosis due to technical errors. Some surgeons feel the proximal anastomosis must have a take-off angle of 45 degrees while other surgeons believe the take-off angle is not critical. In addition, it is generally felt that intima-to-intima contact of the vessels at the anastomosis is advantageous for endothelization to occur, thereby making an ideal union of the vessels. However, intima-to-adventitia contact is acceptable by most surgeons. The main objective of the surgeon is to create an anastomosis with an expected long-term patency rate of greater than 5 to 10 years. The creation of an anastomosis takes approximately 10 to 15 mins.

One essential requirement for creating a sutured anastomosis without error is adequate exposure. Acute visualization of the vessel walls is mandatory in order to properly place each stitch and avoid inadvertently including the back wall of the vessel in a stitch, which in effect narrows or completely occludes the vessel. In order to achieve the required exposure most surgeons will employee blood-less field devices such as shunts, snares, and misted blowers. Further, largely invasive surgical techniques are also employed to help the surgeon gain access to the grafting site. For this reason, CABG surgery is typically performed through a median sternotomy, which provides access to all major coronary branches. A median sternotomy incision begins just below the sternal notch and extends slightly below the xiphoid process. A sternal retractor is used to separate the sternal edges for optimal exposure of the heart. Hemostasis of the sternal edges is typically obtained using electrocautery with a ball-tip electrode and a thin layer of bone wax.

Currently, the golden standard for creation of a vascular anastomosis is manual suturing. Manual suturing may be used to attach vascular grafts (either autografts or prosthetic grafts) for coronary bypass, femoral-femoral bypass (to relieve inadequate circulation in the legs), and AV fistulas and/or shunts (access portals for repeated puncture applications such as kidney dialysis or diabetes). However, a number of cardiac surgical procedures, e.g., off-pump, beating heart CABG procedures, minimally invasive procedures and even totally endoscopic procedures with access through ports only, may require a variety of new anastomotic techniques. The ability of performing anastomoses with limited or no CPB support may increase the possibility of performing more CABG procedures using minimally invasive surgical techniques. Avoiding the use of cross clamps and CPB or dramatically reducing pump run and cross clamp times may effectively minimize post-operative complications. For this reason, there is an increasing need for easier, quicker, less damaging, but reliable automated, semi-automated, or at least facilitated methods to replace or enhance the normal process of a manually sutured vascular anastomosis.

The major objective of any CABG procedure is to perform a technically perfect anastomosis. However, creation of a technically perfect anastomosis is generally complex, tedious, time consuming and its success is highly dependent on a surgeon's skill level. Therefore, creation of vascular anastomoses without the need to perform delicate and intricate suture lines may enable surgeons to more quickly create simpler and effective anastomoses. Currently, there are a number of techniques or procedures being investigated for facilitating the process of forming an anastomosis including vascular clips or staples, glues, adhesives or sealants, laser welding, mechanical couplers, stents and robot-assisted suturing. These techniques are being developed for performing end-to-end, end-to-side and/or side-to-side anastomoses with or without temporary blood flow interruption. In general, these techniques may include the use of various biomaterials and/or biocompatible agents.

There are a number of alternative approaches to CABG surgery. In one approach, the surgeon harvests a graft blood vessel from the patient and prepares its proximal and distal ends to be attached in a "proximal anastomosis" and a "distal anastomosis" bypassing the occlusion. This type of graft is commonly known as a "free" graft. The proximal anastomosis can be located proximal or upstream to the occlusion or to another vessel supplying oxygenated blood, e.g., the aorta. Typically, a section of the saphenous vein or radial artery is harvested from the patient's body and used as a free graft. The opening in the aorta, the aortotomy, is typically made by removing the pericardial layer covering the aorta, creating a small (less than 5 mm) incision through the layers of aortic wall, inserting an aortic punch into the incision and finally actuating the punch to create a round hole. This hole is made into the aorta to provide arterial blood to the bypass graft. To achieve the best flow dynamics, the hole created by the punch should have smooth edges. In addition, the aortic tissue may be very tough to puncture, thereby requiring some effort to produce an acceptable aortotomy.

In another approach, a portion of the left IMA or right IMA is dissected away from supporting tissue and severed so that the severed end can be anastomosed to the obstructed coronary artery distally to the stenosis or occlusion. More recently, other arteries have been used in "attached" graft procedures, including the inferior epigastric arteries and gastroepiploic arteries. It is also stated in U.S. Pat. No. 6,080,175 that a conventional electrosurgical instrument can be introduced through a port or incision and used to dissect and prepare the bypass graft vessel for coronary anastomosis while viewing the procedure through a thoracoscope.

It is necessary to access and prepare the site or sites of the vessel wall of the target coronary artery where the proximal and/or distal anastomosis is to be completed and to then make the surgical attachments of the blood vessels. First, it is necessary to isolate the anastomosis site of the target coronary artery from the epicardial tissues and overlying fatty layers. Typically, blunt, rounded #15 scalpel blades are employed to dissect these tissues and layers away from the target coronary artery.

Generally, blood flow in the target coronary artery is interrupted by, for example, temporary ligation or clamping of the artery proximal and/or distal of the anastomosis site, and the target coronary artery wall is opened to form an arteriotomy, that is, an elongated incision at the anastomosis site extending parallel to the axis of the coronary vessel and equally spaced from the sides of the coronary artery that are still embedded in or against the epicardium. The arteriotomy is typically created by use of a very sharp, pointed, #11 scalpel blade to perforate the coronary artery wall, and the puncture is elongated the requisite length using scissors. A "perfect arteriotomy" is an incision that has straight edges, that does not stray from the axial alignment and equal distance from the sides of the coronary artery, and is of the requisite length.

Similarly, it is necessary to prepare the attachment end of the source vessel by cutting the source vessel end at an appropriate angle for an end-to-side or end-to-end anastomosis or by forming an elongated arteriotomy in the source vessel wall of a suitable length that is axially aligned with the source vessel axis for a side-to-side anastomosis. Typically, the surgeon uses surgical scalpels and scissors to shape the source vessel end or make the elongated arteriotomy slit in the source vessel, and uses sutures or clips to close the open severed end.

In the example depicted schematically in FIG. 1, the heart 12 is prepared as described above for an end-to-side anastomosis of the surgically freed, severed, and appropriately shaped vessel end 31 of the left IMA 30 branching from the aorta 16 and left subclavian artery 18 to the prepared arteriotomy 15 in the vessel wall of the left anterior descending (LAD) coronary artery 14 downstream from the obstruction 38. Similarly, in the example depicted schematically in FIG. 3, the heart 12 is prepared as described above for a side-to-side anastomosis of the left IMA 30 to the prepared arteriotomy 15 in the vessel wall of the LAD coronary artery 14. In the side-to-side anastomosis, an arteriotomy 33 is made in the freed segment of the left IMA 30, and the vessel end 31 is sutured closed. In the example depicted schematically in FIG. 5, the heart 12 is prepared as described above for an end-to-side anastomosis of the surgically harvested, and appropriately shaped vessel end 41 of the free graft 40, e.g., a saphenous vein or radial artery segment, to the prepared arteriotomy 15 in the vessel wall of the LAD coronary artery 14 downstream from the obstruction 38. In addition, the heart 12 is prepared as described above for an end-to-side anastomosis of the appropriately shaped vessel end 42 of the free graft 40 to the prepared aortotomy 43 in the wall of the aorta 16.

The prepared end or elongated arteriotomy of a bypass graft or source vessel is attached or anastomosed to the target coronary artery or aorta at the arteriotomy or aortotomy in a manner that prevents leakage of blood employing sutures, staples, surgical adhesives and/or various artificial anastomosis devices. For example, an end-to-side anastomosis 35 of the shaped vessel end 31 of the left IMA 30 to the prepared arteriotomy 15 in the vessel wall of the LAD coronary artery 14 is illustrated in FIG. 2. And a side-to-side anastomosis 37 joining the arteriotomy 33 of the left IMA 30 to the prepared arteriotomy 15 of the LAD coronary artery 14 is illustrated, for example, in FIG. 4. And an end-to-side anastomosis 35 of the shaped vessel end 41 of the free graft 40 to the prepared arteriotomy 15 in the vessel wall of the LAD coronary artery 14 is illustrated in FIG. 6. In addition, an end-to-side anastomosis 47 of the shaped vessel end 42 of the free graft 40 to the prepared aortotomy 43 in the wall of the aorta 16 is also illustrated in FIG. 6. Alternatively, anastomoses 35 and 47 may be constructed as side-to-side anastomoses, if so desired.

The inner, endothelial layer, vessel linings are less thrombogenic than the outer epithelial layers of blood vessels. So, in one approach, the attachment is made by everting and applying the interior linings of the bypass graft or source vessel and the target coronary artery against one another and suturing or gluing or otherwise attaching the interior linings together. Various types of artificial biocompatible reinforcement sleeves or rings may also be used in the anastomosis. Currently, a number of mechanical anastomotic devices, materials, techniques, and procedures are being developed for facilitating the process of forming an anastomosis including vascular clips or staples, glues, adhesives or sealants, laser welding, mechanical couplers, stents and robot-assisted suturing. These techniques are being developed for performing end-to-end, end-to-side and/or side-to-side anastomoses with or without temporary blood flow interruption. In general, these techniques can include the use of various biomaterials and/or biocompatible agents. See, for example, U.S. Pat. Nos. 5,385,606, 5,695,504, 5,707,380, 5,972,017 and 5,976,178, and 6,231,565.

Various examples of forming the target vessel arteriotomy or arteriotomies, the shaped end or side wall arteriotomy of the source vessel, and the positioning and attachment of the source vessel and target artery together are set forth in U.S.

Pat. Nos. 5,776,154, 5,799,661, 5,868,770, 5,893,369, 6,026, 814, 6,071,295, 6,080,175, 6,248,117, 6,331,158, and 6,332, 468.

In a conventional bypass graft or CABG procedure, the surgeon exposes the obstructed coronary vessel through an open chest surgical exposure or stemotomy providing direct visualization and access to the epicardium. Typically, fat layers that make it difficult to see either the artery or the occlusion cover the epicardial surface and the obstructed cardiac artery. However, surgeons are able to dissect the fat away to expose the artery and manually palpate the heart to feel the relatively stiff or rigid occlusion within the artery as a result of their training and experience. The surgeon can determine the location and length of the occlusion as well as suitable sites of the target coronary artery for the proximal and distal anastomoses with some degree of success.

The open chest procedure involves making a 20 to 25 cm incision in the chest of the patient, severing the sternum and cutting and peeling back various layers of tissue in order to give access to the heart and arterial sources. As a result, these operations typically require large numbers of sutures or staples to close the incision and 5 to 10 wire hooks to keep the severed sternum together. Such surgery often carries additional complications such as instability of the sternum, post-operative bleeding, and mediastinal infection. The thoracic muscle and ribs are also severely traumatized, and the healing process results in an unattractive scar. Post-operatively, most patients endure significant pain and must forego work or strenuous activity for a long recovery period.

Many minimally invasive surgical techniques and devices have been introduced in order to reduce the risk of morbidity, expense, trauma, patient mortality, infection, and other complications associated with open chest cardiac surgery. Less traumatic limited open chest techniques using an abdominal (sub-xyphoid) approach or, alternatively, a "Chamberlain" incision (an approximately 8 cm incision at the stemocostal junction), have been developed to lessen the operating area and the associated complications. In recent years, a growing number of surgeons have begun performing CABG procedures while the heart is still beating using minimally invasive direct coronary artery bypass grafting (MIDCAB) surgical techniques and devices. Using the MIDCAB method, the heart typically is accessed through a mini-thoracotomy (i.e., a 6 to 8 cm incision in the patient's chest between the ribs) that avoids the sternal splitting incision of conventional cardiac surgery. A MIDCAB technique for performing a CABG procedure is described in U.S. Pat. No. 5,875,782, for example.

Other minimally invasive, percutaneous, coronary surgical procedures have been advanced that employ multiple small trans-thoracic incisions to and through the pericardium, instruments advanced through sleeves or ports inserted in the incisions, and a thoracoscope to view the accessed cardiac site while the procedure is performed as shown, for example, in the above-referenced '175, '295, '468 and '661 patents and in U.S. Pat. Nos. 5,464,447, and 5,716,392. Surgical trocars having a diameter of about 3 mm to 15 mm are fitted into lumens of tubular trocar sleeves or ports, and the assemblies are inserted into skin incisions. The trocar tip is advanced to puncture the abdomen or chest to reach the pericardium, and the trocar is then withdrawn leaving the port in place. Surgical instruments and other devices such as fiber optic thoracoscopes can be inserted into the body cavity through the port lumens. As stated in the '468 patent, instruments advanced through trocars can include electrosurgical tools, graspers, forceps, scalpels, electrocautery devices, clip appliers, scissors, etc.

In an endoscopic approach, the surgeon may stop the heart by utilizing a series of internal catheters to stop blood flow through the aorta and to administer cardioplegia solution. The endoscopic approach utilizes groin cannulation to establish CPB and an intraaortic balloon catheter that functions as an internal aortic clamp by means of an expandable balloon at its distal end is used to occlude blood flow in the ascending aorta. A full description of an example of one preferred endoscopic technique is found in U.S. Pat. No. 5,452,733, for example.

In an attempt to eliminate problems associated with CPB, "beating heart" procedures that eliminate the need for CPB have been developed. Surgical instruments that attempt to stabilize or immobilize a portion of the beating heart that supports the target coronary artery and the anastomosis site have been developed. These beating heart procedures and instruments described, for example, in the above-referenced '158, '175, '770, '782, and '295 patents and in U.S. Pat. Nos. 5,976,069, and 6,120,436, can be performed on a heart exposed in a full or limited thoracotomy or accessed percutaneously.

For example, a retractor assembly disclosed in the above-referenced '158 patent mounts to and maintains the chest opening while supporting a stabilizer assembly that extends parallel stabilizer bars against the epicardium alongside the target coronary artery so that force is applied across the anastomosis site to suppress heart motion. The surgeon employs conventional manually applied clamps to block blood flow through the arterial lumen and scalpels and scissors to make the elongated incision of the arteriotomy.

Instruments are disclosed in the above-referenced '295 patent that apply suction to the epicardial surface around or alongside the anastomosis site to suppress heart motion. Again, the surgeon employs the conventional manually applied clamps to block blood flow through the arterial lumen and a scalpel to make the elongated incision of the arteriotomy.

Beating heart surgical methods still use clamps and thus, still present the problems associated with clamps described above. For example, the common practice in beating heart surgical methods is to use a side-clamp rather than a cross-clamp. Beating heart surgical methods still require the creation of anastomosis and thus still require an aortotomy. Thus beating heart surgical methods still present the time constraints and difficulties associated with creating an effective anastomosis, such as difficulty creating an aortotomy hole with smooth edges and potential trauma resulting from clamping.

Several attempts have been made to create devices that occlude the vessel without using clamps or devices that maintain hemostasis of the aortotomy or arteriotomy during creation of an anastomosis.

U.S. Pat. Nos. 6,132,397 and 6,068,608 to Davis describes an aortic arch clamp catheter which occludes the ascending aorta using an expandable balloon rather than a cross clamp.

U.S. Pat. No. 6,165,196 to Stack et al. describes an occlusion apparatus with two occluding members and a shield that resists perforation.

U.S. Pat. No. 5,766,151 to Valley et al. describes a modified endovascularly inserted, internal vascular clamp to be used within the vessel instead of the external cross clamp.

Other methods and devices are described for creating effective anastomoses.

U.S. Pat. No. 6,193,734 to Bolduc et al. describes a device for creating anastomoses using a tissue securing member movable from a first to second configuration which movement causes a compressive force to be applied to the vessels to be joined.

U.S. Pat. No. 6,234,995 to Peacock describes a modified arterial catheter with a distal end portion that may be positioned within the aortic root adjacent to the left ventricle and a proximal portion that is coupled to a bypass pump.

U.S. Pat. No. 6,395,015 to Borst et al. and assigned to Medtronic describes a temporary intravascular arteriotomy seal for insertion into and retrieval from a blood vessel through an opening in the wall of the vessel.

U.S. Pat. No. 6,171,319 to Nobles and Baladi describes a device comprising an inverting member adapted to be inserted through a small incision in a blood vessel while the inverting member is maintained in an elongated, narrow configuration. A seal is then formed by applying a proximal force to the inverting member which has been inverted into an expanded, inward-facing cup following insertion into the blood vessel. The rim of the cup forms a seal against the inner wall of the blood vessel, thereby preventing blood from flowing out of the incision.

Instruments that combine the application of suction to the epicardial surface around or alongside the anastomosis site to suppress heart motion with a cutting mechanism for making the arteriotomy are disclosed in the above-referenced '175 and '770 patents. The surgical cutting instruments disclosed in the '770 and '175 patents include an elongated shaft having a proximal end, a distal end adapted for percutaneous insertion against the target coronary artery over the anastomosis site, and an axial lumen therebetween. A suction pad is formed at the distal end of the shaft, and a cutting element disposed within the lumen of the shaft near the distal end. A vacuum line is fluidly coupled to the lumen of the shaft and is adapted to connect to a vacuum source to effect a suction force at the distal end of the shaft. A control mechanism is provided to selectively block flow between the vacuum source and the lumen. The control mechanism may include a slide valve, an on/off button, or other equivalent mechanism for selectively closing and opening the vacuum pathway. A gripper assembly configured to grip a portion of the coronary artery is also disclosed in the '175 patent.

The cutting element and the shaft are relatively moveable between a retracted position and a cutting position. The cutting element is adapted to make the elongated slit of the arteriotomy in alignment with the axis of the coronary artery when the cutting element and the shaft are in the cutting position and the vacuum holds the anastomosis site steady.

The distal end of the shaft disclosed in the '175 patent has an outside diameter of less than about 5 mm, and the cutting element comprises at least one cutting element having a substantially straight blade cutting edge. The cutting edge is displaced at an angle of between about 15 to 30 degrees relative to a vertical axis through the cutting element. In one embodiment, the cutting element is fixed to an actuator push rod located within the lumen of the shaft, and connected to an actuator, preferably an actuator button, at a proximal end thereof. In another embodiment, the shaft is slidably mounted to a handle of the cutting instrument. An anchor, preferably a rigid rod coaxially disposed within the shaft, fixes the cutting element to the handle. An actuator member mounted to the shaft and biased by a spring is actuated to slide the shaft between retracted and cutting positions with respect to the cutting element.

Additionally or alternatively, at least one electrode may be disposed near the distal end of the shaft to effect or enhance cutting. The electrode may be operatively coupled to the cutting element, preferably substantially co-linearly coupled to the cutting edge. In the depicted embodiments, the electrode extends to the sharpened tip of the cutting element opposite to the cutting blade. In use, the end of the electrode at the tip of the cutting element is placed against the coronary artery and energized by radio frequency energy as the cutting element is moved to the cutting position to facilitate making a small point incision or pilot hole in the coronary artery. Then, the cutting blade is fully advanced to make the elongated cut. Ultrasonic energy may be applied to the cutting element to effect or enhance cutting by the ultrasonically vibrating the cutting blade.

The approaches described above for making an arteriotomy employ a cutting blade to make the elongated slit. In most cases, the shaft must be carefully moved to advance the cutting blade along the length of the vessel wall without inadvertently pushing the tip of blade across the vessel lumen and through the vessel wall opposite to the intended slit. Damage can be caused to the vessel wall if care is not taken.

An instrument or tool is needed for making an arteriotomy, an aortotomy or a similar incision in a vessel wall that avoids or minimizes the loss of blood through the incision.

An instrument or tool is needed that inhibits blood loss through the incision as an anastomosis is being made.

An instrument or tool is needed that reduces or eliminates the need for clamps.

An instrument or tool is also needed that reduces the time for creating an anastomosis.

All the publications and patents described above are hereby incorporated by reference herein in their respective entireties. As those of ordinary skill in the art will appreciate readily upon reading the Summary of the Invention, the Detailed Description of the Preferred Embodiments and the Claims set forth below, many of the devices and methods disclosed above may be modified advantageously by using the teachings of the present invention.

SUMMARY OF THE INVENTION

The present invention is preferably embodied in methods and devices for creating and sealing openings in vessels, e.g., coronary arteries. In accordance with one aspect of the present invention a device for creating an opening in a first blood vessel and for sealing the opening in the first blood vessel while an anastomosis is created between the first blood vessel and a second blood vessel comprises a cutting mechanism for creating the opening in the first blood vessel and a seal for sealing the opening in the first blood vessel. In one embodiment of the present invention, the cutting mechanism comprises one or more electrodes.

In accordance with another aspect of the present invention a method of constructing an anastomosis between a first vessel and a second vessel comprises a device having a cutting mechanism for creating an opening in a vessel and a seal for sealing the opening in the vessel. In one embodiment of the present invention, the cutting mechanism comprises one or more electrodes that can be used to form an opening in the vessel. In one embodiment of the present invention, the seal may be delivered in a first configuration into the opening in a vessel. The seal may also be deployed to a second configuration to seal the opening.

In accordance with one aspect of the present invention a method and device for performing the method of making an opening into a vessel of a patient comprises accessing the outer surface of the vessel wall, applying a ground electrode in contact with the body of the patient, applying an electrosurgical cutting electrode to the outer surface of the vessel wall and applying RF energy between the electrosurgical cutting electrode and the ground electrode at an energy level and for a duration sufficient to cut an opening through the vessel wall where the electrosurgical cutting electrode is applied to the outer surface of the vessel wall.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

FIG. 8a is a schematic diagram of one embodiment of an occluding device in a first configuration for use in accordance with the present invention;

FIG. 8b is a schematic diagram of the occluding device of FIG. 8a in a second configuration for use in accordance with the present invention;

FIG. 19 is a schematic diagram of one embodiment of a vessel sealing device in accordance with the present invention;

DETAILED DESCRIPTION OF THE PREFERRED EMBODIMENTS

Figure 1:
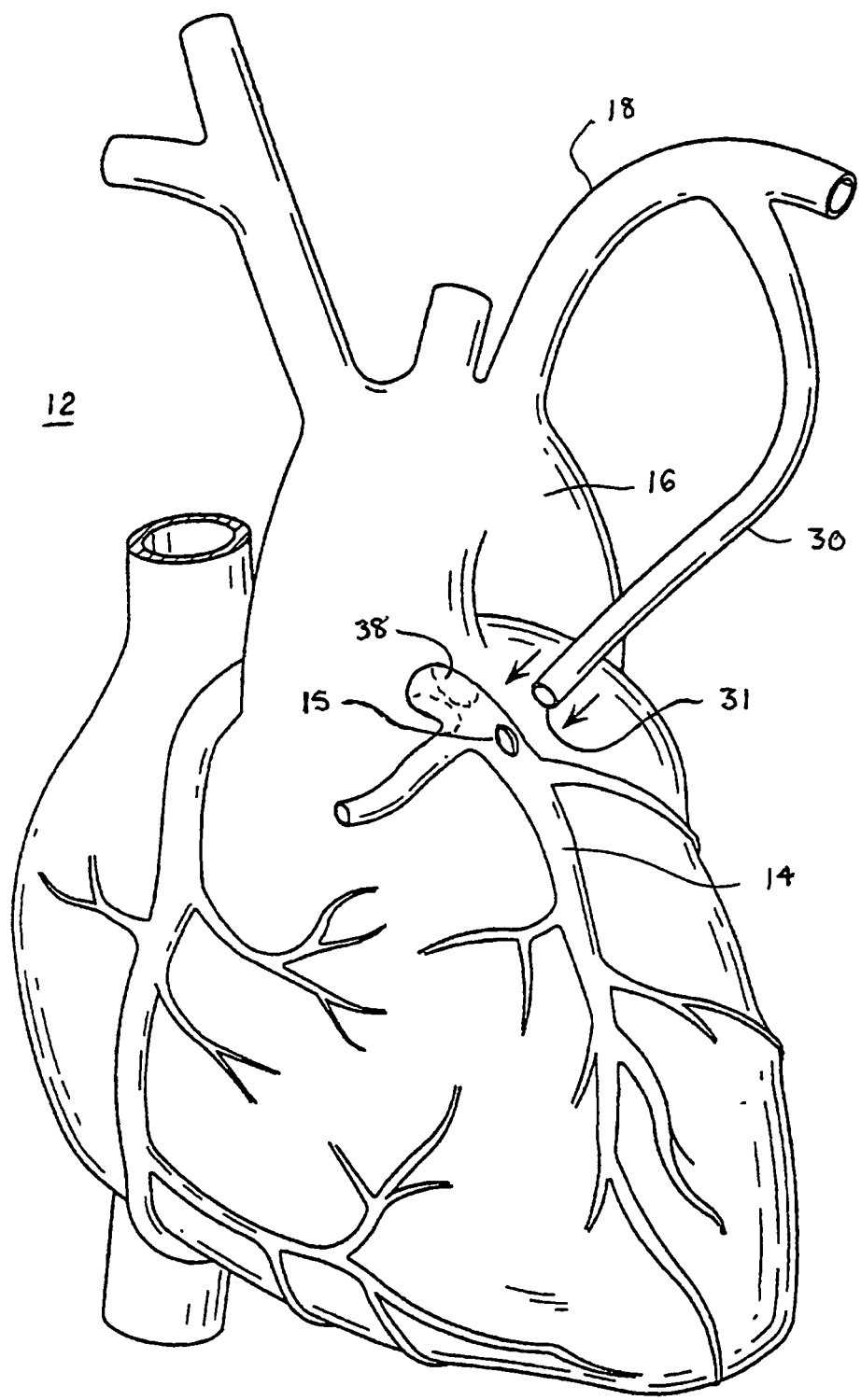
FIG. 1 is a schematic illustration of the preparation of a source vessel free end and an arteriotomy in a coronary artery downstream from an obstruction for an end-to-side anastomosis.
Figure 2:
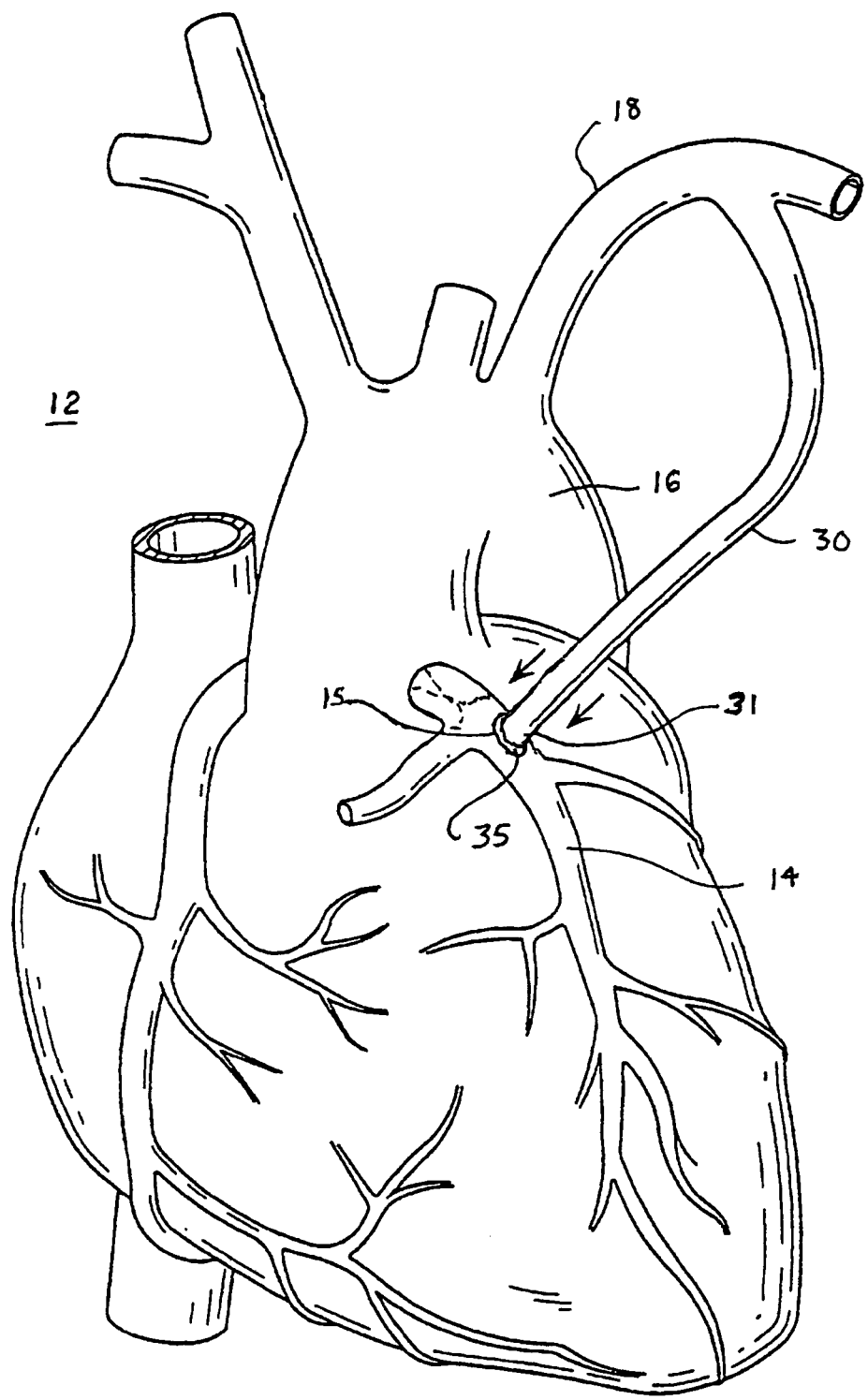
FIG. 2 is a schematic illustration of the end-to-side anastomosis of the source vessel free end to the arteriotomy in the coronary artery.
Figure 3:
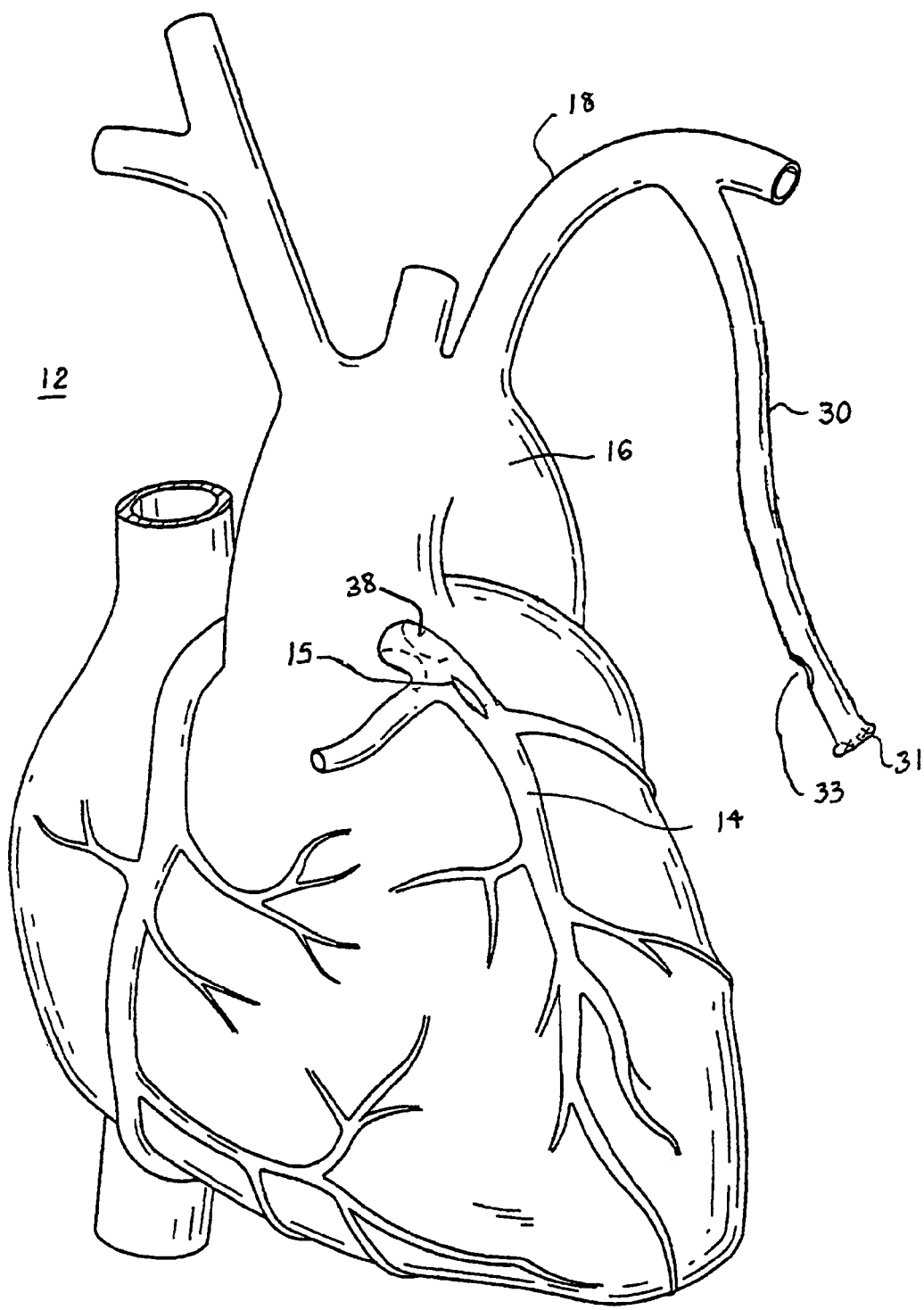
FIG. 3 is a schematic illustration of the preparation of a source vessel free end and an arteriotomy in a coronary artery downstream from an obstruction for a side-to-side anastomosis.
Figure 4:
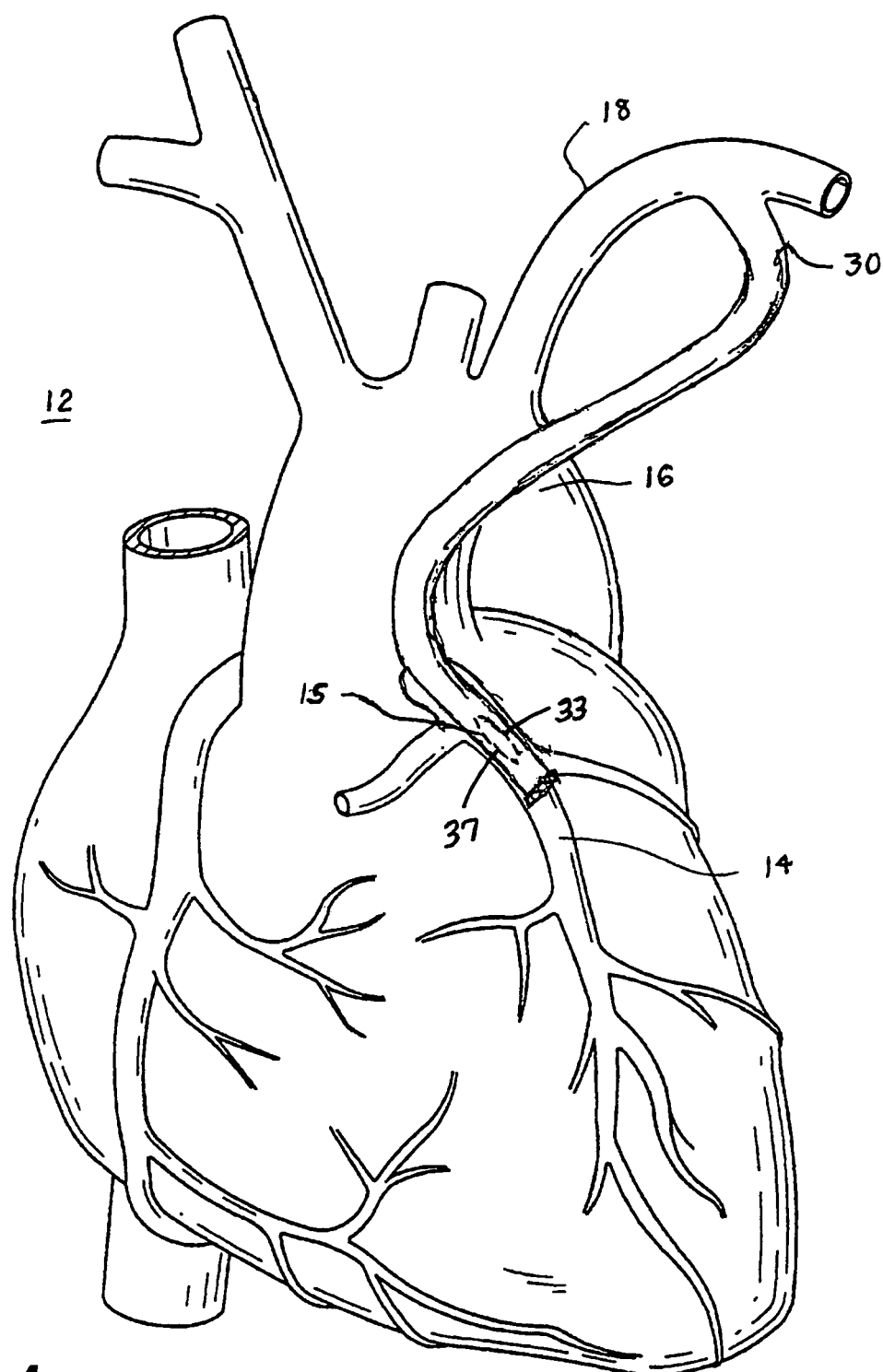
FIG. 4 is a schematic illustration of the side-to-side anastomosis of the arteriotomy in the source vessel to the arteriotomy in the coronary artery.
Figure 5:
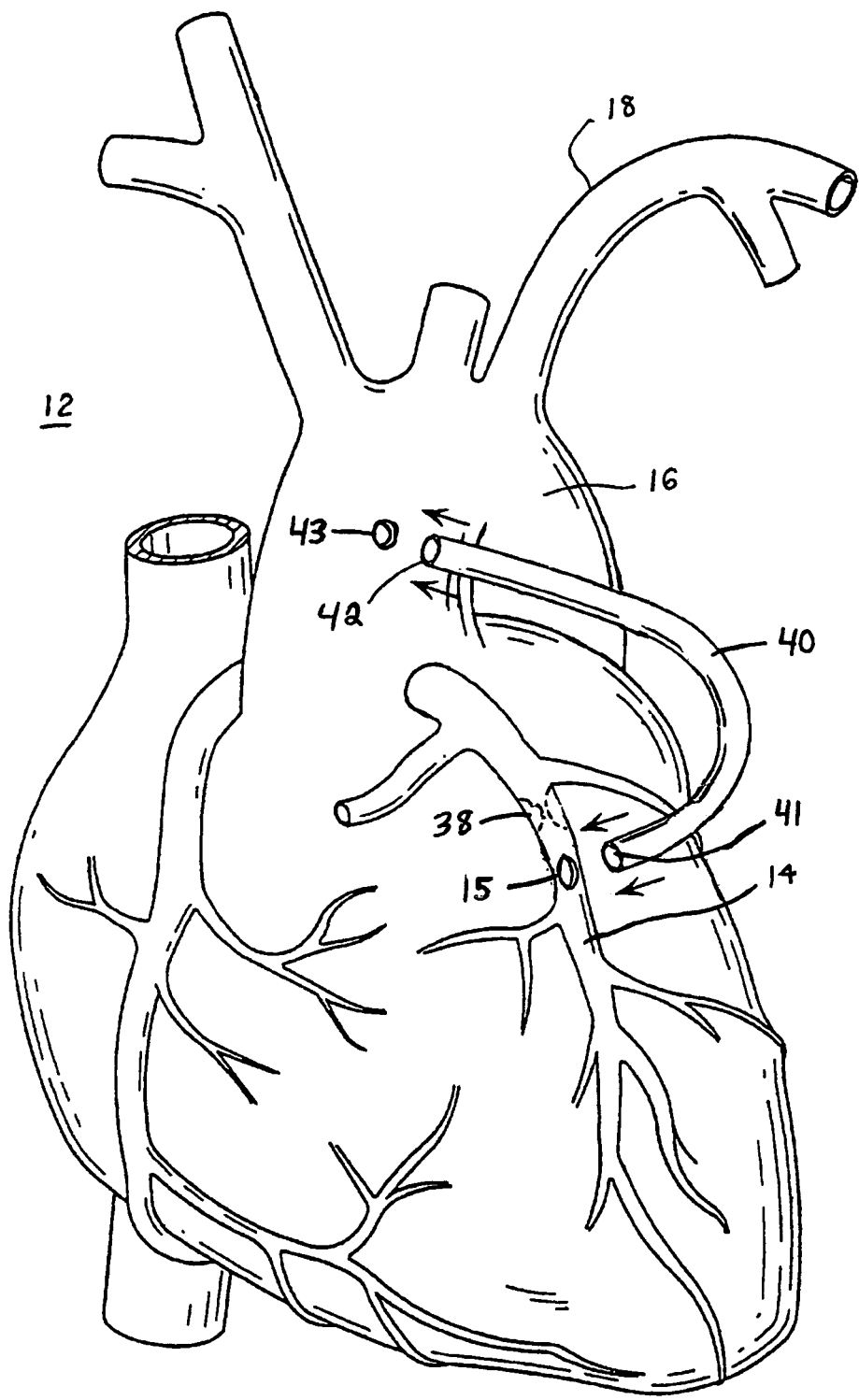
FIG. 5 is a schematic illustration of the preparation of the ends of a free graft and an arteriotomy in a coronary artery downstream from an obstruction for an end-to-side anastomosis and an aortotomy in the wall of an aorta.
Figure 6:
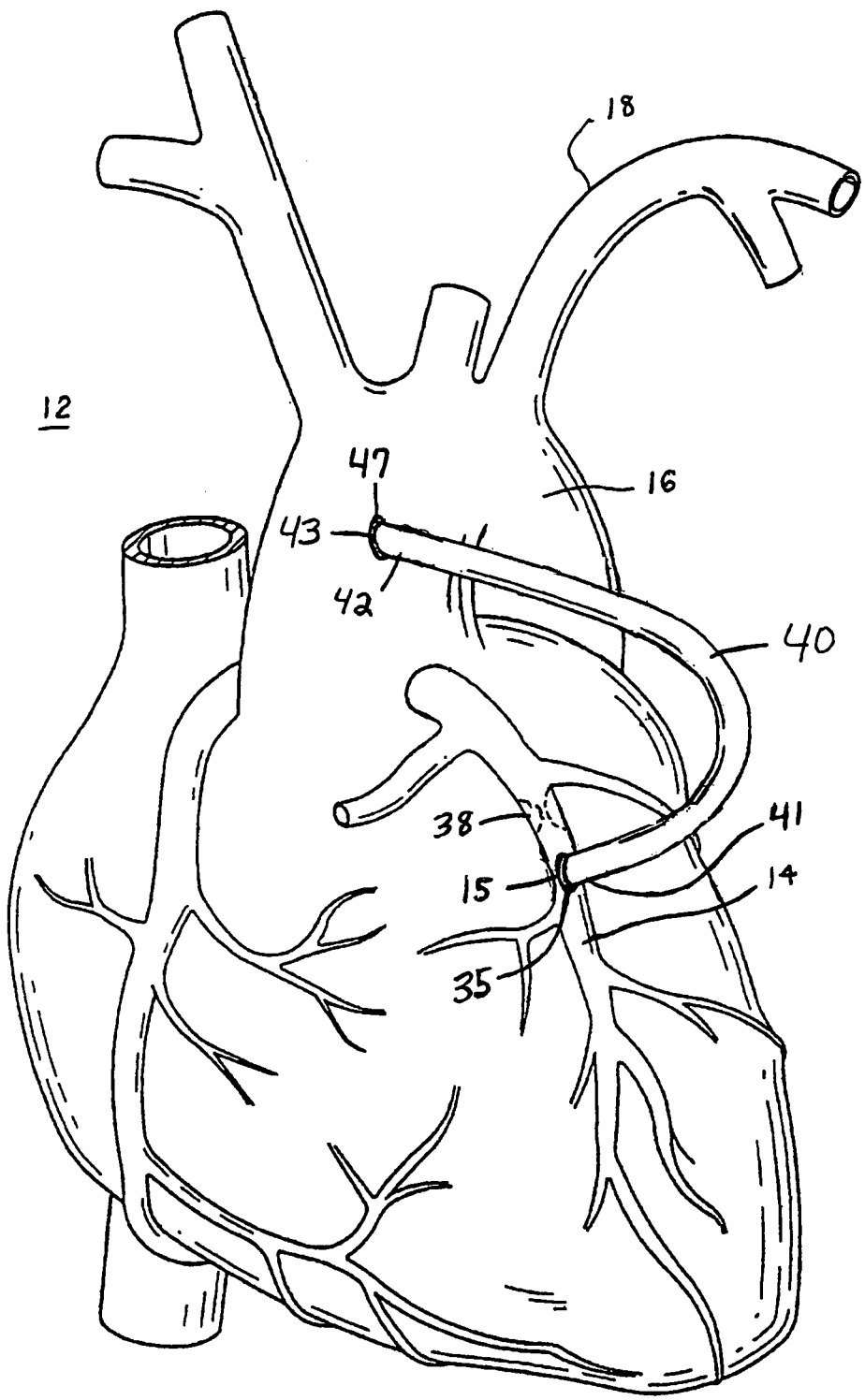
FIG. 6 is a schematic illustration of the end-to-side anastomosis of one end of the free graft to the arteriotomy in the coronary artery and the end-to-side anastomosis of the other end of the free graft to the aortotomy in the aorta.

In the following detailed description, references are made to illustrative embodiments for carrying out the invention. It is understood that other embodiments may be utilized without departing from the scope of the invention.

For example, while a preferred method of forming arteriotomies in coronary arteries and aortotomies in the aorta in the process of performing anastomoses in a CABG procedure will be described herein, it is to be understood that the principles of the present invention may be applied to a wide variety of surgical procedures, both conventional procedures, as well as minimally invasive procedures.

Vessel sealing devices or instruments of the present invention, for example, may comprise elements for forming arteriotomies and/or aortotomies in vessel walls through the passage of a radio frequency (RF) energy between an active cutting electrode applied to the vessel wall and a ground pad contacting the patient's skin or a ground electrode introduced into the vessel lumen. The RF energy or current cuts tissue at the active cutting electrode, the cutting rate being dependent on current density through the tissue contacted by the active cutting electrode. Rapid, clean edge incisions are made through the vessel wall when current density exceeds a threshold that causes the fluid within the cells to turn to steam, creating a sufficient overpressure so as to burst the cell walls. The cells then dry up, desiccate, and carbonize, resulting in localized shrinking and an opening in the tissue.

Current density depends upon the area the active cutting electrode presents to the vessel wall, the series impedance, typically resistance, to current flow between the active and ground pad or ground electrode, and the voltage applied to the series impedance. Current density is inversely proportional to active electrode contact area, so current density increases as active electrode surface area decreases. The current density is typically adjusted by varying the voltage applied to the active electrode since the area of a particular electrosurgical instrument active electrode is fixed and the series impedance cannot always be controlled.

The series impedance is dependent upon several factors including the material and design of the active cutting electrode, the type, thickness and conductivity of tissue and fluid between the active cutting electrode and the ground pad or electrode, the intimacy of contact of the cutting electrode with the tissue to be cut, and the location of the grounding pad or electrode relative to the cutting electrode. RF energy generators used in this type of surgery have a wide range of power output to accommodate a variety of procedures and devices. For example, the RF energy generator can be adjusted to either cut tissue or to merely cauterize previously cut or torn tissue.

The objective in electrosurgical tissue cutting is to heat the cells of the tissue so rapidly that they explode into steam leaving a cavity in the cell matrix. The heat is meant to be dissipated in the steam and not to dry out adjacent cells. When the electrode is moved and fresh tissue is contacted, new cells are exploded, and the incision is made or continued. The electrical current utilized in electrosurgical cutting is in the radio frequency range and operates by jumping across an air gap to the tissue. This is commonly referred to as sparking. An explanation of electrosurgical cutting theory can be found in the FORCE 1 Instruction Manual published by Valleylab, Inc. of Boulder, Colo., and dated Mar. 1, 1986.

In accordance with the present invention, instruments and methods are provided that can be used in any of the above described full exposure surgical procedures or less invasive MIDCAB or percutaneous exposures of the vessels in question, particularly, the above-described CABG procedures on a stopped or beating heart.

Figure 7:
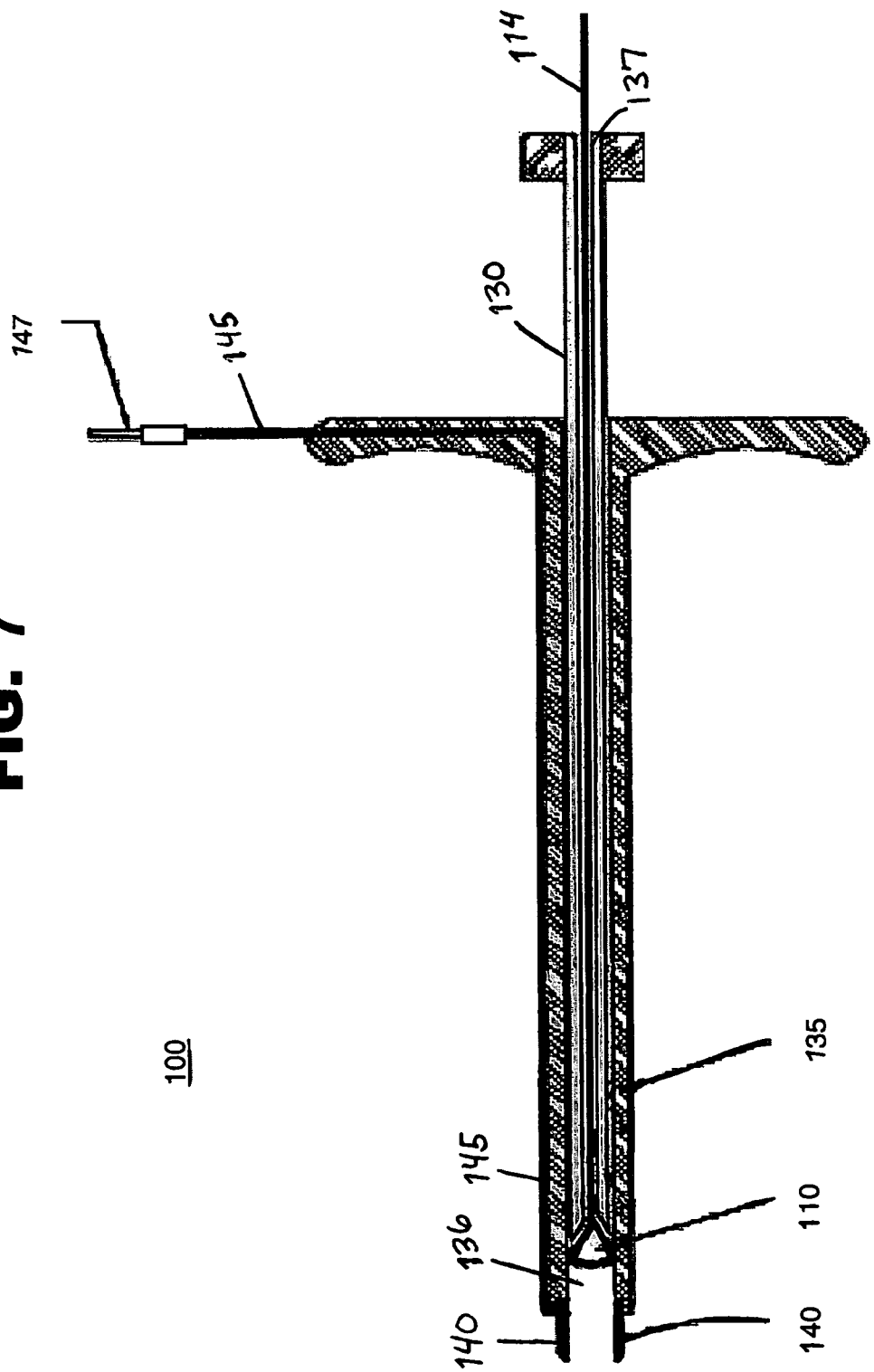
FIG. 7 is a schematic diagram of one embodiment of a vessel sealing device in accordance with the present invention.

FIG. 7 shows one embodiment of a vessel sealing device in accordance with the present invention at 100. Vessel sealing device 100 comprises a cutting mechanism 140 located at the proximal end of device 100. Cutting mechanism 140 is used to create an incision or opening in a vessel wall through which occluding device or seal 110 and tether 114 are delivered. As seen in FIG. 7, some embodiments of vessel sealing device 100 comprise elements that enable sealing device 100 to use electrical energy, e.g., RF energy, or other suitable energy. For example, in FIG. 7 cutting mechanism 140 comprises an electrode. Vessel sealing device 100 further comprises a power conductor 145 to conduct power to cutting electrode 140. Power conductor 145 may be connected to a power source by power connector pin 147. As described above, delivery shaft 130 is used to deliver seal 110 and seal tether 114 through and out of inner lumen 136 of tool body 135. Prior to delivery of seal 110, tether 114 resides in lumen 137 of shaft 130. In addition, cutting mechanism 140 is fixed to the proximal end of tool body 135. Preferably shaft 130 and tool body 135 are made of one or more non-conductive materials.

Power conductor 145 may be any suitable power conductor for delivering sufficient energy to cutting mechanism 140. For example, power conductor 145 may comprise one or more metal wires. Power connector pin 147 may be any suitable connector that connects conductor 145 to a suitable power source.

FIGS. 8a and 8b show one embodiment of a seal 110 for use in accordance with the present invention. For example, seal 110 may be used with vessel sealing device 100. As seen by comparing FIGS. 8a and 8b, seal 110 may be constructed so that it is deployed in the configuration of FIG. 8a and then, once placed, attains the configuration shown in FIG. 8b.

Seal 110 may be formed of any suitable biocompatible material, for example, a biocompatible polymer, which is impervious to blood. A biocompatible material would prompt little allergenic response and would be resistant to corrosion when placed within the patient's body. Alternatively, seal 110 may be a material of suitable flexibility, which is coated with a biocompatible coating.

In one embodiment of the invention, seal 110 may be comprised of a flexible sheet material. The sheet material of seal 110 is sufficiently flexible such that its width dimensions can be made sufficiently small by folding along ribs 112 to fit through an opening in a vessel, such as opening created by cutting mechanism 140.

The dimensions of seal 110 of the present invention may be determined, for example, by the vessel into which the seal is inserted and the size and purpose of the opening or incision to be sealed. A seal 110 of a given size and configuration may fit different sizes of vessels and openings within a certain range, e.g. for coronary artery bypass grafting. FIGS. 8a and 8b show a round seal 110 particularly suitable for use in sealing a round opening, e.g., a round aortotomy. However, an oval seal configuration may be more suited for sealing an elongated opening, e.g., an elongated arteriotomy.

As shown in FIGS. 8a and 8b, seal 110 may comprise ribs 112. Ribs 112 may also be formed of suitable biocompatible material such as, for example, a biocompatible metal or polymer, which is impervious to blood. A biocompatible material would prompt little allergenic response and would be resistant to corrosion when placed within the patient's body. Alternatively, ribs 112 may be made of material of suitable rigidity, which is coated with a biocompatible coating.

Ribs 112 may be formed of one or more materials that are more rigid than the seal 110, for example, ribs 112 may be made of metal, e.g., stainless steel or nitinol, while seal 110 may be made of flexible plastic, e.g., silicone rubber or polyurethane.

The dimensions of ribs 112 may be determined based on the dimensions of seal 110. For example, as seen in FIGS. 8a and 8b, ribs 112 are the same length as the length of seal 110. However, in one embodiment of the invention, ribs 112 may be smaller in dimension than seal 110.

Ribs 112 may provide additional rigidity to seal 110 following placement of seal 110. Although in the embodiment of FIG. 8b, ribs 112 are shown in an "X" configuration on seal 110, ribs 112 may be formed in any suitable configuration on seal 110, such as a plurality of ribs radiating outward on seal 110 like the ribs of an umbrella.

When placed in the configuration shown in FIG. 8b, ribs 112 may be used with seal tether 114 to help manipulate seal 110 and/or to shape seal 110 into a desired configuration, such as the deployment configuration of FIG. 8a. The flexible sheet material of seal 110 will easily fold in the direction Fb when seal tether 114 is pulled in direction Fa. This allows for easy insertion and retrieval of seal 110 through an opening in the vessel wall. On the other hand, the flexible sheet material of seal 110 has a natural tendency to unfold and appose the vessel wall adjacent to the puncture once seal tether 114 is released.

Seal tether 114 may be formed of any suitable biocompatible material as is known in the art. For example, seal tether 114 may be constructed of suture material of appropriate strength so that the material may be pulled to fold seal 110 as described above. Alternatively, seal tether 114 may be constructed of biocompatible wire.

As described above, seal delivery shaft 130 may be used to introduce seal 110 into the vessel. In the embodiment of FIG. 7, delivery shaft 130 is preferably made of a suitable biocompatible material as discussed above.

Figure 9:
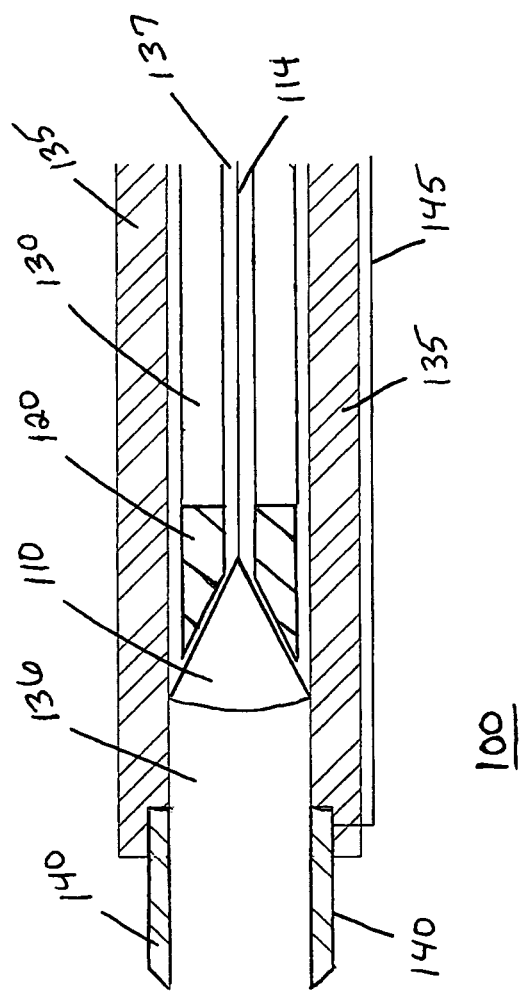
FIG. 9 is a schematic diagram of one embodiment of a vessel sealing device in accordance with the present invention.

In one embodiment, a seal delivery head 120 (see FIG. 9) may be used in conjunction with seal delivery shaft 130 to introduce seal 110 into the vessel. For example, seal delivery head 120 may be used to help guide seal 110 through tool body lumen 136. Seal delivery head 120 may be made of a suitable biocompatible material as described above. Seal delivery head 120 may be, for example, fixed or coupled onto shaft 130 and can be used to help deploy seal 110 into the opening in the wall of the target vessel. Seal delivery head 120 may also be constructed of any of the many surgically acceptable materials, for example, various polymers or plastics, stainless steels, nitinol, cobalt alloys, and other iron or nickel containing alloys or titanium.

As seen by comparing FIGS. 8a and 8b, seal 110 may be constructed so that it is deployed in the configuration of FIG. 8a and then, once placed, attains the configuration shown in FIG. 8b. This is further illustrated in FIGS. 10 and 11.

Figure 10:
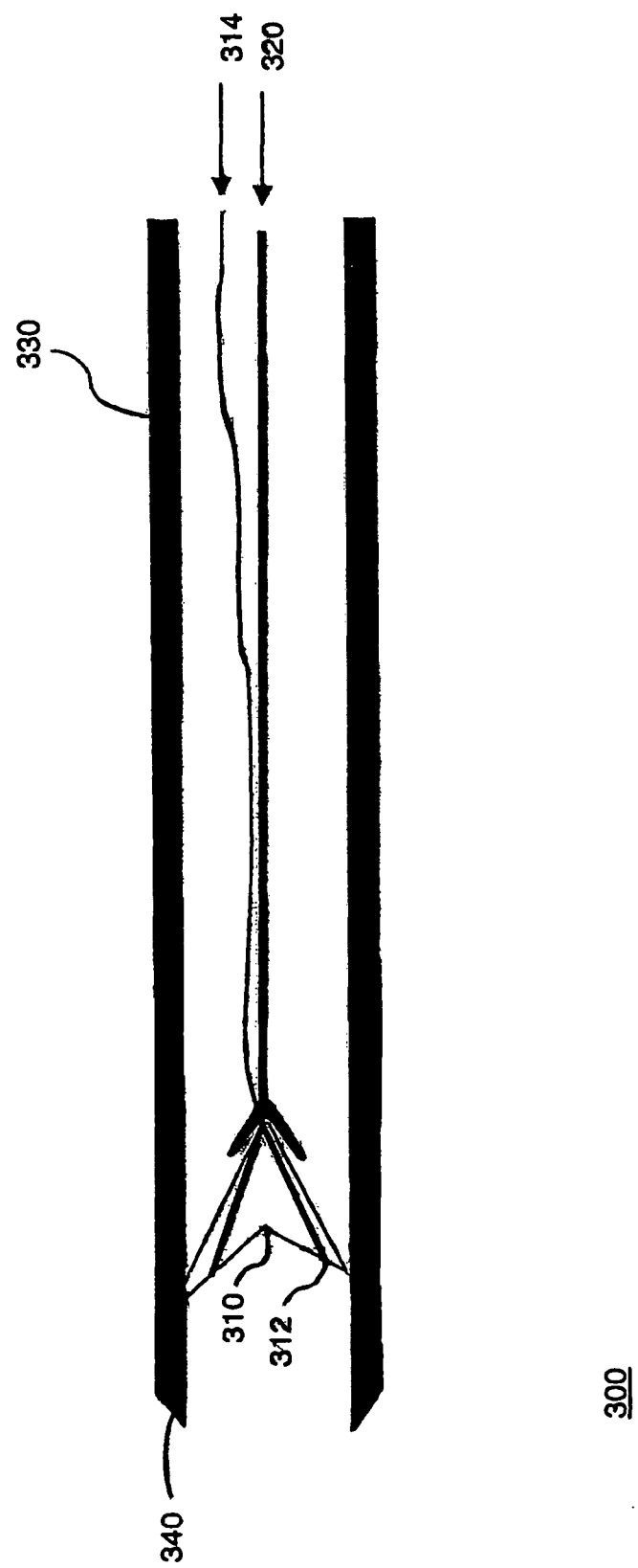
FIG. 10 is a schematic diagram of one embodiment of a vessel sealing device in accordance with the present invention.

FIG. 10 shows the proximal end of one embodiment of a vessel sealing device in accordance with the present invention at 300. Vessel sealing device 300 comprises cutting mechanism 340, which is used to manually create a puncture or opening in the recipient vessel. Alternatively, cutting mechanism 140 described above may be used in sealing device 300 to create the opening in the wall of the vessel. Cutting mechanism 340 is attached to tool body 330. Alternatively, tool body 330 may comprise a blunt end at its proximal end instead of cutting mechanism 140. A device 300 that has a blunt ended tool body 330 would be inserted into an existing incision or opening, for example, an arteriotomy or aortotomy. For example, the opening in the vessel may have been made by a conventional cutting means such as a scalpel or tissue punch. Delivery shaft 320 is used to push seal 310 and tether 314 through and out of the inner lumen of tool body 330. In one embodiment, delivery shaft 320 may be configured as a push rod made of one or more biocompatible materials which may or may not be non-conductive.

Figure 11:
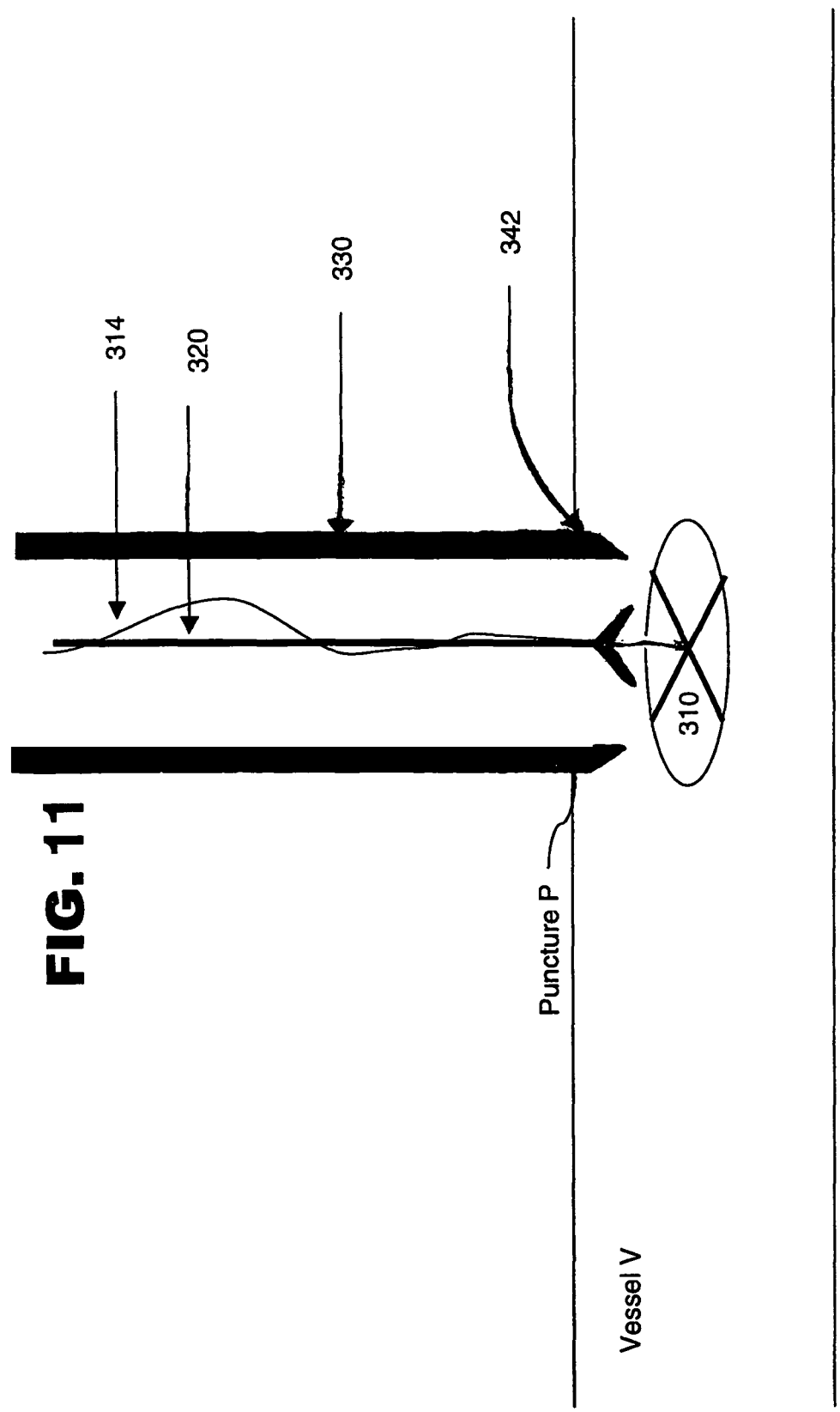
FIG. 11 is a schematic diagram of one embodiment of a vessel sealing device in accordance with the present invention.

FIG. 11 shows the embodiment of sealing device 300 in situ. Cutting mechanism 340 may comprise one or more cutting members 342. Cutting mechanism 340 and cutting members 342 may be made of suitable biocompatible materials capable of creating a puncture in a vessel. Any of the many surgically acceptable materials may be used such as various stainless steels, cobalt alloys, and other iron or nickel containing alloys or titanium. Tool body 330 may also be made of one or more biocompatible or surgically acceptable materials. As seen in FIG. 11, cutting members 342 are used to create the puncture P in vessel V. Once the cutting members 342 and, in one embodiment, a portion of tool body 330 have been inserted through puncture P and into vessel V, seal 310 may be delivered through inner lumen of tool body 330 by pushing delivery shaft 320. When seal 310 is in place, seal 310 is released from delivery shaft 320 so that seal 310 deploys to an appropriate configuration for sealing puncture P in vessel V. After introduction into the vessel, the blood pressure will sealingly engage seal 310 with the inside of the wall of the vessel in the vicinity of the puncture P (not shown). Once in the proper place, the transmural pressure in the vessel will keep seal 310 neatly apposed to the inner vessel wall, thereby sealing the puncture or incision. The graft vessel may then be attached to the recipient vessel. Once the anastomosis is almost complete, seal 310 may be removed by pulling on tether 314. Upon removal of seal 310, the anastomosis may be completed. Alternatively, seal 310 may be made of a dissolvable biocompatible material so it may be left in a sealing position while the anastomosis is completed. A dissolvable seal 310 may then be allowed to dissolve away in the blood stream.

Figure 12:
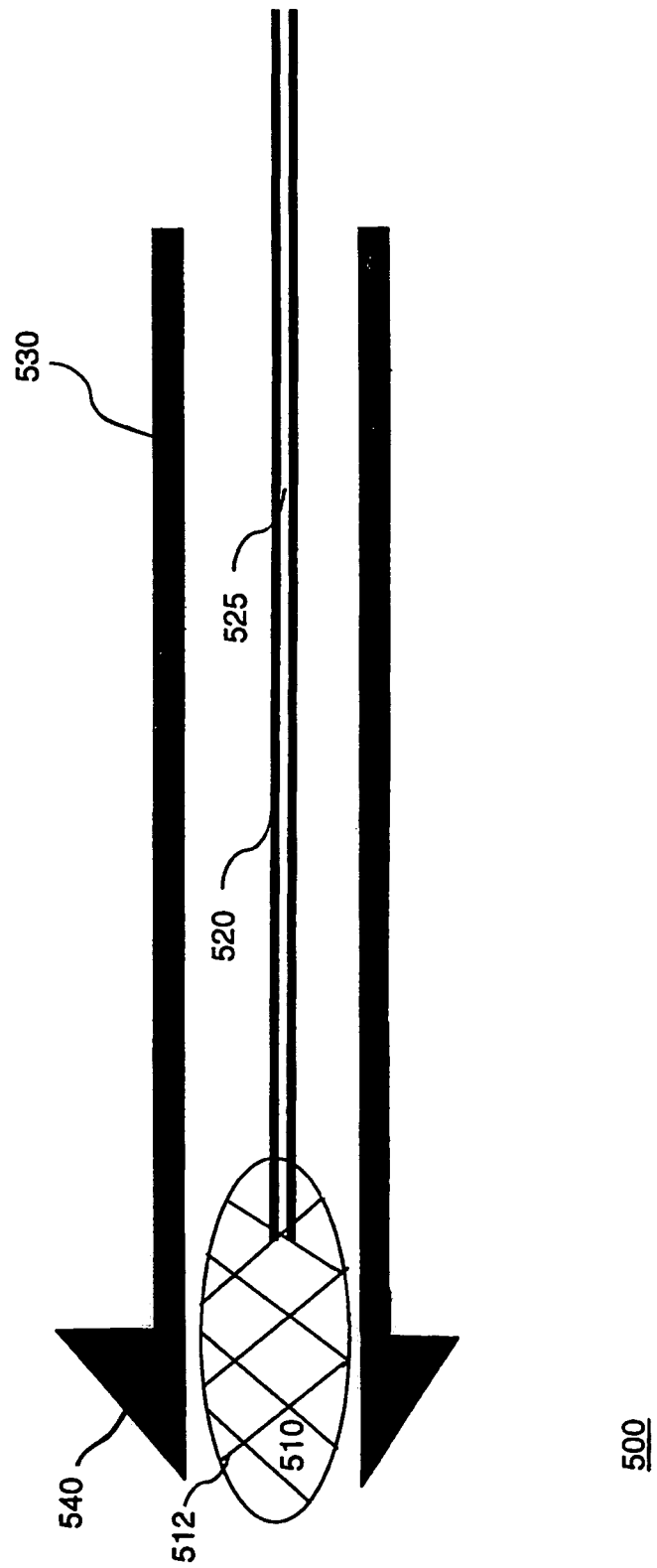
FIG. 12 is a schematic diagram of one embodiment of a vessel sealing device in accordance with the present invention.

FIG. 12 shows another embodiment of a vessel sealing device in accordance with the present invention at 500. Vessel sealing device 500 comprises a cutting mechanism 540, which is used to manually create a puncture or hole in the recipient vessel. Alternatively, cutting mechanisms 140 or 340 described above may be used in sealing device 500 to create the opening in the recipient vessel. Cutting mechanism 540 is attached to tool body 530. Seal 510 may be delivered through the inner lumen of tool body 530 by pushing on the rigid tether 520. Seal 510 may be an inflatable seal. In FIG. 12, seal 520 is shown in a partially deflated state. Tether 520 may comprise an inner lumen 525 through which seal 510 may be inflated.

Seal 510 may comprise microscopic pores, thereby allowing seal 510 to function as local delivery device. For example, local heparin may be delivered through lumen 525 to seal 510. Heparin is then delivered from seal 510 to the anastomosis site thereby reducing the risk of clot formation and local intimal hyperplasia. The local delivery of heparin may reduce or even abolish any need for anti-coagulation during anastomosis suturing. Obviating the need for systemic anti-platelet therapy and/or anticoagulation may contribute to a reduction in any bleeding problems. Seal 510 may be designed to deliver one or more agents, e.g., therapeutic agents, medical agents, biological agents, drugs and/or cells.

Similar to earlier embodiments of the present invention, one or more components of sealing device 500 may be made of one or more biocompatible materials. Further, one or more components of sealing device 500 may be coated with one or more biological agents, e.g., an anti-coagulation agent such as heparin. The coatings may be hydrophilic or hydrophobic as desired.

Inflatable seal 510 may comprise one or more ribs 512 used to provide rigidity and/or fluid delivery. For example ribs 512 may have inner lumens and one or more fluid openings for fluid delivery. Inner lumens of ribs 512 may be fluidly connected to one or more lumens of tether 520, e.g., lumen 525. Seal 510 may be inflated by introduction of a fluid, such as saline, through inner lumen 525 of tether 520.

Seal 510 may comprise one or more shapes inflated and/or deflated. For example, in one embodiment seal 510 may have a round inflated shape. Alternatively, seal 510 may have an oval inflated shape. The overall shape of seal 510 may change between an inflated shape and a deflated shape. For example, seal 510 may have a round shape when inflated and an elongated shape when deflated. Seal 510 may comprise one or more inflatable chambers or balloons each having similar or different shapes. Inflation and deflation of the one or more chambers or balloons of seal 510 may be accomplished via one or more lumens of tether 520. Each chamber or balloon may be fluidly connected to a separate lumen or a single lumen may be fluidly connected to two or more chambers or balloons.

Figure 13:
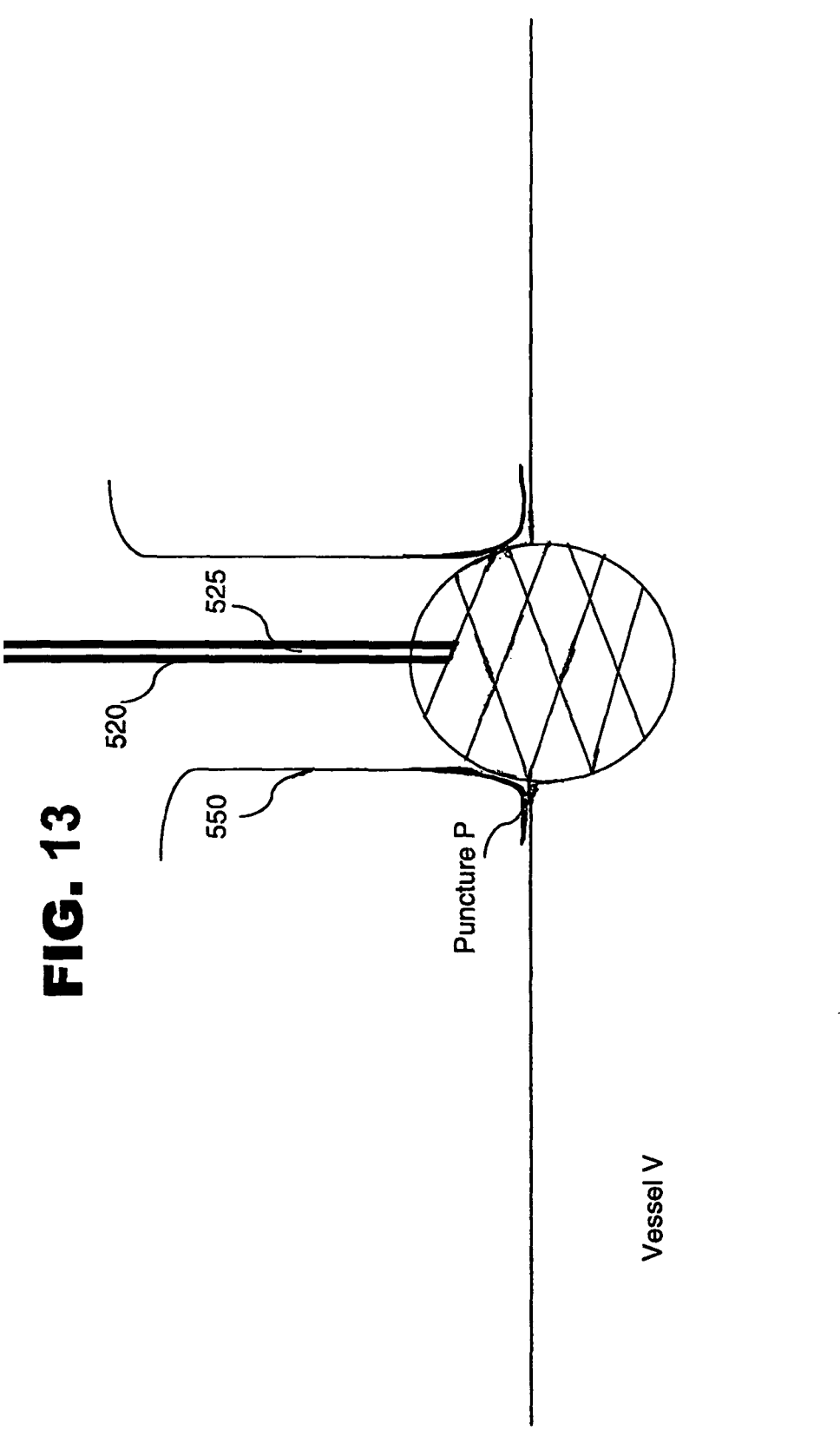
FIG. 13 is a schematic diagram of one embodiment of a vessel sealing device in accordance with the present invention.

FIG. 13 shows an embodiment of seal 510 in situ. Cutting mechanism 540 is used to create a puncture P in vessel V. Once the cutting mechanism 540 has been inserted within the vessel, seal 510 may be delivered through tool body 530 by pushing on rigid tether 520. Following insertion and placement of seal 510, tool body 530 may be removed. When seal 510 is in place, fluid may be delivered through inner lumen 525 of tether 520 to inflate seal 510. After introduction into the vessel, the blood pressure will sealingly engage seal 510 with the inside of the wall of the vessel in the vicinity of the puncture P. Seal 510 is relatively compliant and apposes the wall of vessel V. In its inflated state, seal 510 preferably creates a minimal cross-sectional area (minimal obstruction to flow). Depending on the inflation pressure, the inflatable seal 510 adjusts to the radius of curvature of the vessel and seals the opening in the vessel. Graft vessel 550 may then be placed over tether 520 and attached to the recipient vessel V. Once the anastomosis is completed, seal 510 may be deflated and removed through the lumen of graft vessel 550.

In some embodiments of the invention, sutures and suture needles for completing the anastomosis may guided into proper position by suture guides located on the surface of seal 510 (not shown). In some embodiments of the invention, the material of seal 510 may be compliant, such that the material of seal 510 gives way to a suture needle, for example, thereby allowing the suture needle to be passed through graft vessel 550, along the surface of seal 510, and through vessel V, without puncturing seal 510 and producing a leak. The material of seal 510 may be designed to prevent punctures by suture needles or other sharp objects used in an anastomosis procedure.

In one embodiment of the invention, an opening is made in the recipient vessel using conventional means, e.g., a scalpel and/or a tissue punch such as an aortic punch. A deflated seal 510 may then be placed in the opening. Seal 510 is then inflated to form a fluid tight seal between the balloon and the vessel opening edges. A graft vessel is then positioned adjacent the opening in recipient vessel. Sutures are then placed to fasten the graft vessel to the recipient vessel. Seal 510 may then be removed prior tightening of one or more sutures or following the completion of the anastomosis. The seal may be removed through the lumen of the graft vessel. Alternatively, the seal may be removed between the graft vessel and the recipient vessel prior to the tightening of one or more of the sutures used to connect the graft vessel to the recipient vessel.

Figure 14:
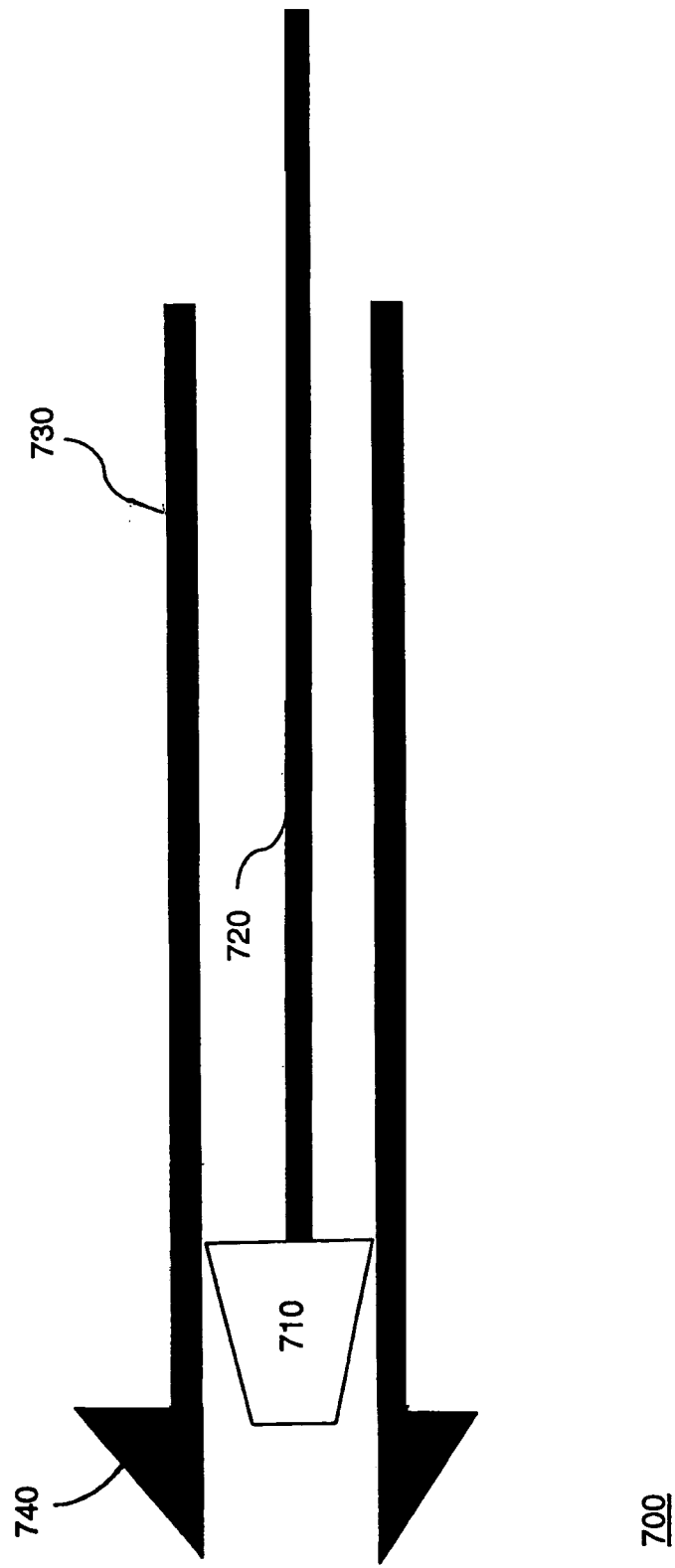
FIG. 14 is a schematic diagram of one embodiment of a vessel sealing device in accordance with the present invention.

FIG. 14 shows yet another embodiment of a vessel sealing device in accordance with the present invention at 700. Vessel sealing device 700 comprises a cutting or puncturing mechanism 740, which is used to manually create an opening in the recipient vessel. Alternatively, the cutting mechanisms or puncturing mechanisms described above may be used in sealing device 700 to create the opening in the recipient vessel. Cutting mechanism 740 is attached to tool body 730. Seal 710 may be delivered through the inner lumen of tool body 730 by pushing on the rigid tether 720. Seal 710 may be a "cork-like" seal of a desired rigidity. Similar to the first embodiment of the present invention, tool body 730, tether 720 and seal 710 may be made of one or more biocompatible materials and/or coatings which may be non-thrombogenic and/or hydrophilic.

Figure 15:
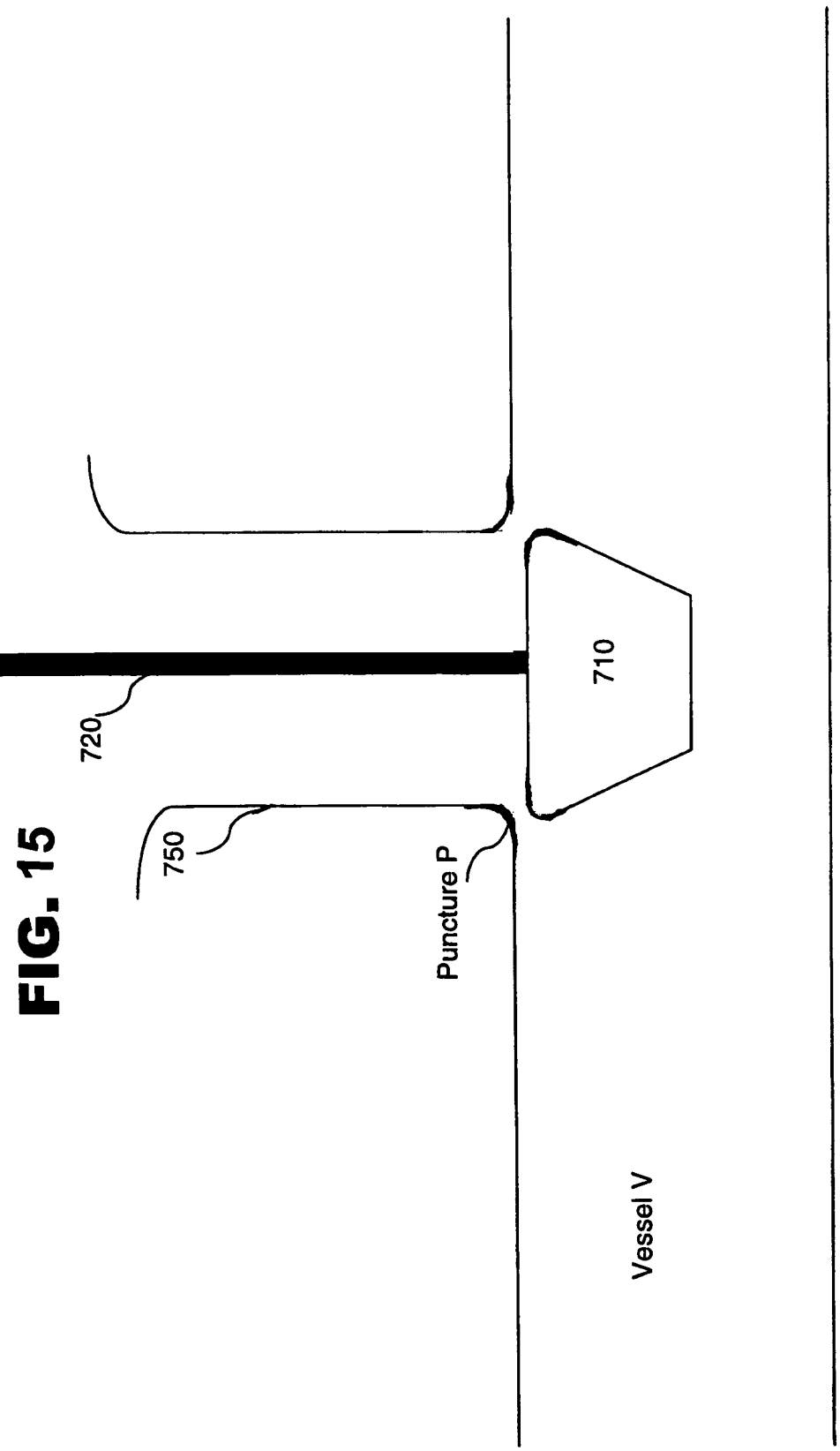
FIG. 15 is a schematic diagram of one embodiment of a vessel sealing device in accordance with the present invention.

FIG. 15 shows an embodiment of sealing device 700 in situ. Seal 710 may comprise a cork-like member or plug. Cutting mechanism 740 may be used to create the opening or puncture P in vessel V. Once the cutting mechanism 740 has been inserted within the vessel, seal 710 may be delivered through tool body 730 by pushing on rigid tether 720. After introduction into the vessel, the blood pressure will sealingly engage seal 710 with the inside of the wall of the vessel in the vicinity of the puncture P. The graft vessel 750 may then be placed over tether 720 and attached or anastomosed to the recipient vessel. Once graft attachment is completed, seal 710 may be removed.

Figure 16:
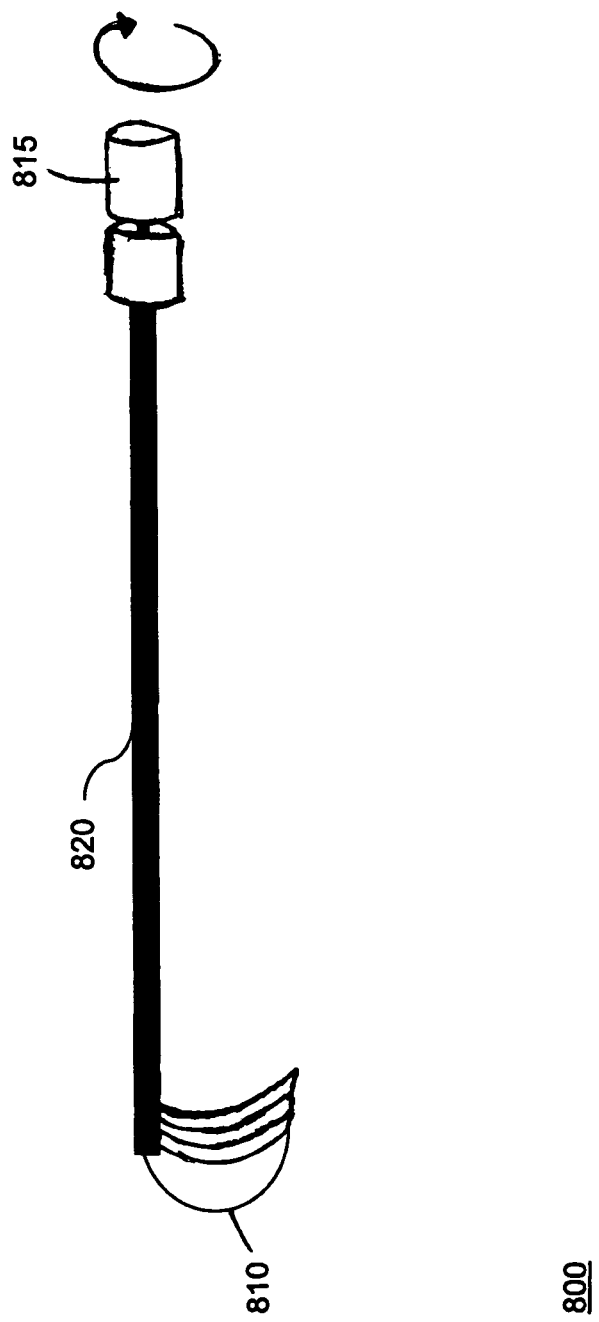
FIG. 16 is a schematic diagram of one embodiment of a vessel sealing device in accordance with the present invention.
Figure 18:
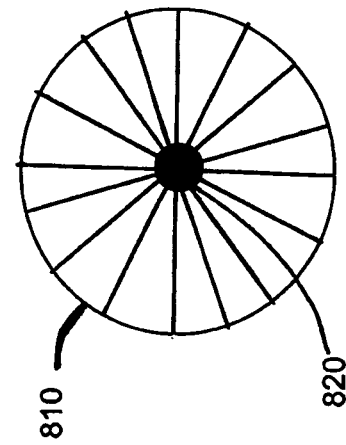
FIG. 18 is a schematic diagram of one embodiment of a vessel sealing device in accordance with the present invention.
Figure 17:
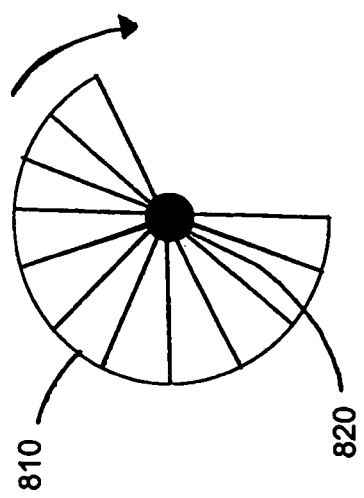
FIG. 17 is a schematic diagram of one embodiment of a vessel sealing device in accordance with the present invention.

FIG. 16 shows another embodiment of a vessel sealing device in accordance with the present invention at 800. Vessel sealing device 800 comprises a plurality of "petals," "blades" or sealing members 810 which are used in combination to seal an opening in a vessel or organ. Sealing members 810 are coupled to shaft 820. FIG. 16 shows a plurality of Sealing members 810 stacked in a delivery configuration, e.g., one on top of another. Following placement of sealing members 810 within an opening in a vessel, sealing members 810 may be "fanned out" thereby sealing the opening from fluid loss. FIG. 17 shows sealing members 810 in a partially fanned out configuration, whereas FIG. 18 shows sealing members 810 in a completely fanned out configuration. Rotation of handle 815 which is coupled to shaft 820 and sealing members 810 in one direction causes sealing members 810 to fan out while rotation of handle 815 in the opposite direction causes sealing members 810 to stack on each other. Sealing members 810 and shaft 820 may be made of one or more suitable biocompatible or surgically acceptable materials as discussed above.

FIG. 19 shows the embodiment of sealing device 800 in situ. Following the creation of an opening in vessel V, i.e., puncture P, sealing members 810 are passed through puncture P and into vessel V. Sealing members 810 are then deployed or fanned out in an appropriate configuration for sealing the vessel as shown in FIG. 19. After introduction into the vessel, the blood pressure will sealingly engage sealing members 810 with the inside of the wall of the vessel in the vicinity of the puncture P. Once in the proper position and configuration, the transmural pressure in the vessel will keep the configured sealing members neatly apposed to the inner vessel wall, thereby sealing the opening, e.g., an arteriotomy or aortotomy. Once the opening is sealed, the graft vessel 850 may be attached to the recipient vessel V. Once the anastomosis is completed, shaft 820 and sealing members 810 may be removed through the graft vessel.

Figure 20:
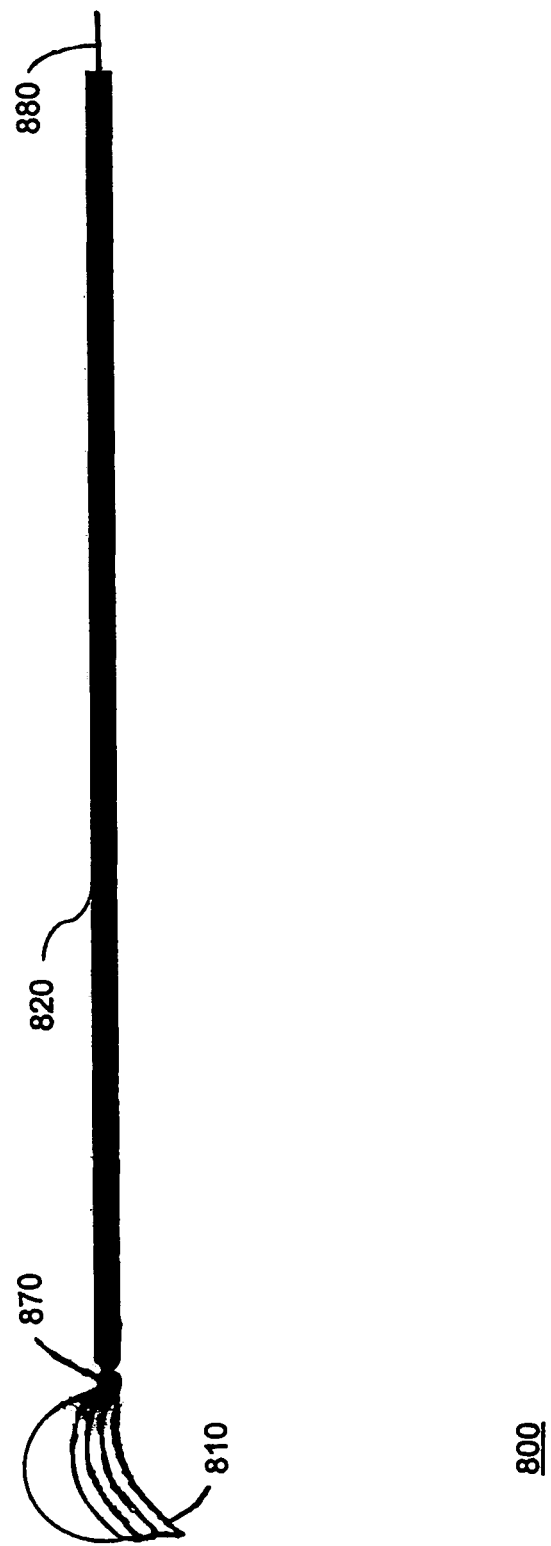
FIG. 20 is a schematic diagram of one embodiment of a vessel sealing device in accordance with the present invention.

FIG. 20 shows an alternative embodiment of vessel sealing device 800 in which vessel sealing device 800 includes a pivot, hinge or joint 870 for articulating or moving sealing members 810 relative to shaft 820. Hinge 870 may be actuated remotely, for example, via a cable or push rod 880.

Figure 21:
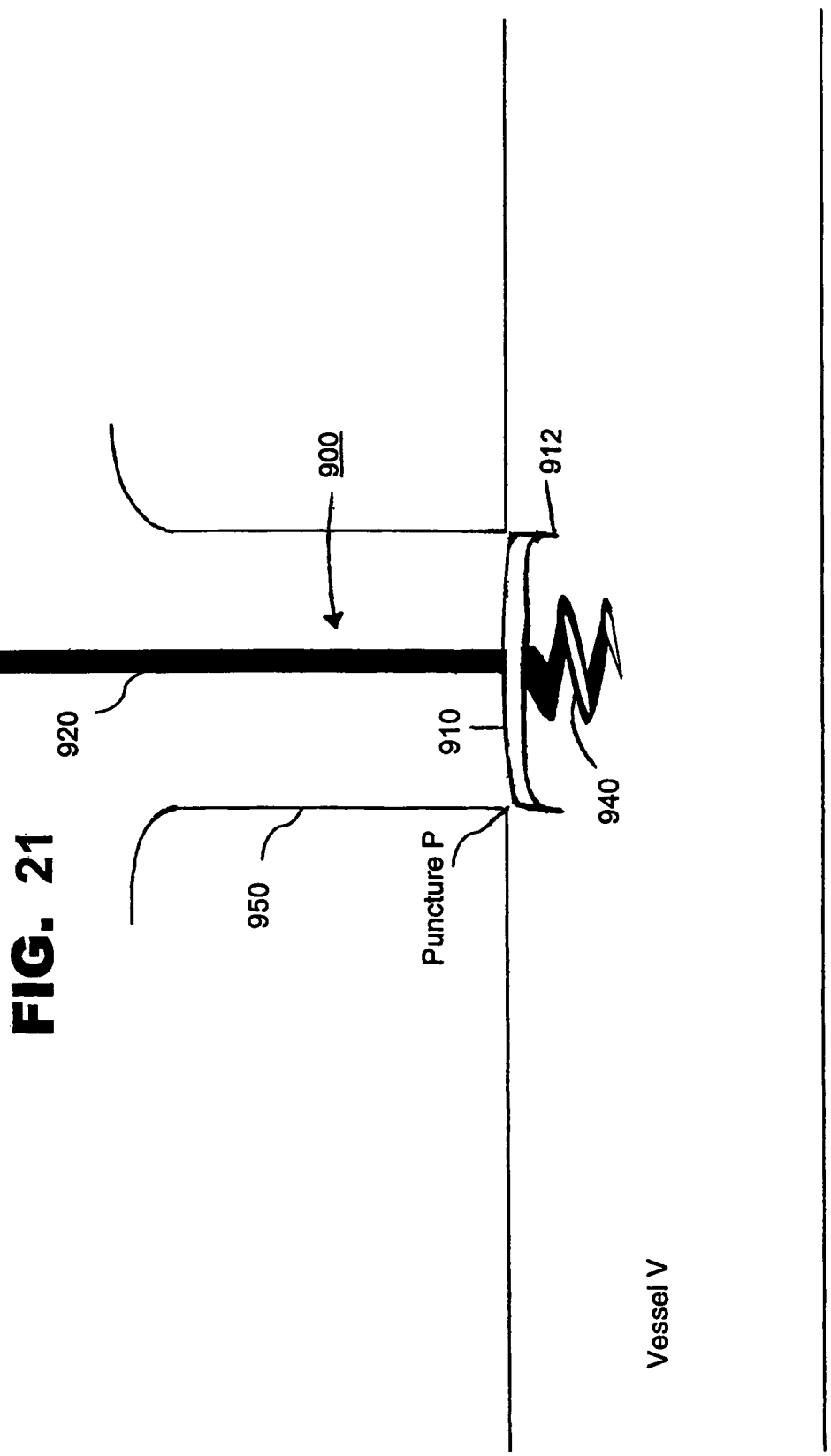
FIG. 21 is a schematic diagram of one embodiment of a vessel sealing device in accordance with the present invention.

FIG. 21 shows another embodiment of a vessel sealing device in situ in accordance with the present invention at 900. Vessel sealing device 900 comprises a sealing member 910 and a corkscrew 940, which are used to manually create an opening or puncture in the recipient vessel and to seal the opening. In one embodiment, sealing member 910 includes one or more cutting blades 912. Corkscrew 940 is located distal to sealing member 910 on shaft 920. Sealing member 910, corkscrew 940 and shaft 920 may comprise or be made of one or more suitable biocompatible or surgically acceptable materials and/or coatings. Any of the many surgically acceptable materials may be used such as various plastics, stainless steels, cobalt alloys, and other iron or nickel containing alloys or titanium. Sealing member may be flexible or compliant enough to be inserted or removed through a vessel.

Corkscrew 940 is screwed into the recipient vessel. Corkscrew 940 may be screwed until cutting blades 912 cut through the recipient vessel wall, thereby forming an opening or puncture. Once the blade has been used to create the opening, sealing member 910 may be left in place to seal the vessel. The graft vessel 950 may then be placed over shaft 920 and attached to the recipient vessel V. Once the anastomosis is completed, corkscrew 940 and sealing member 910 may be removed through the graft vessel.

Figure 22:
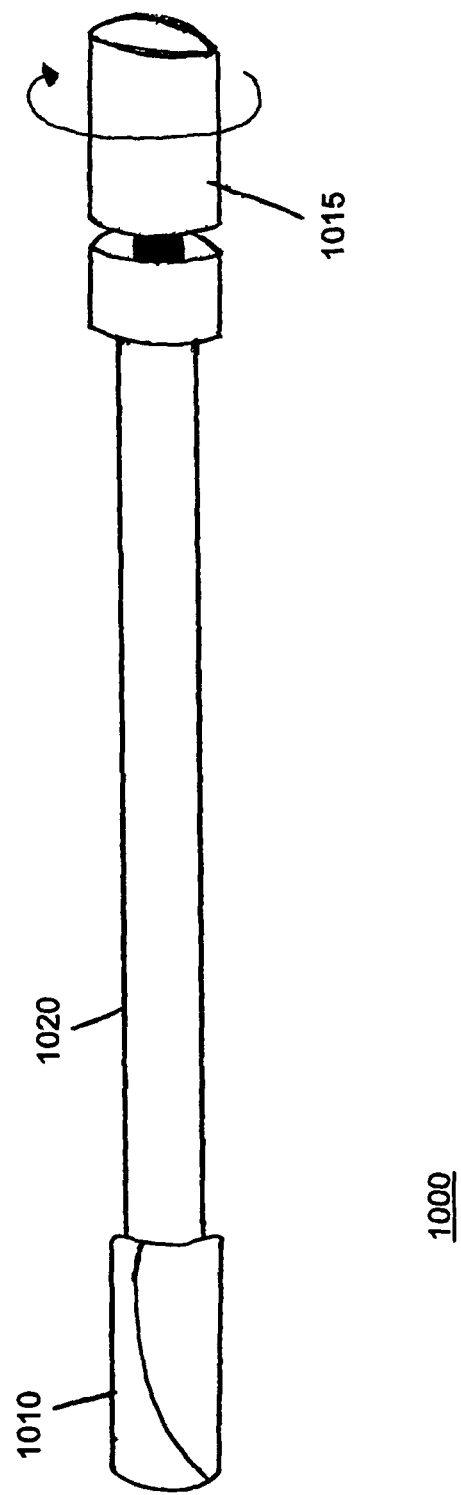
FIG. 22 is a schematic diagram of one embodiment of a vessel sealing device in accordance with the present invention.

FIG. 22 shows another embodiment of a vessel sealing device in accordance with the present invention at 1000. Vessel sealing device 1000 comprises a sealing member 1010 which is used to seal an opening in a vessel or organ, especially during the formation of an anastomosis. Sealing member 1010 is coupled to shaft 1020 and handle 1015. The vessel sealing device allows a surgeon to create an anastomosis between two vessels, e.g., between a graft vessel and an aorta vessel, without using a clamp, e.g., a side-biting clamp. The device may be fed through the conduit or graft vessel, passed thru the opening or puncture in the recipient vessel, e.g., the aorta, and then deployed within the aorta, thereby sealing the opening. The surgeon or an assistant may apply "backpressure" to help occlude the hole. The surgeon can then pass a suture needle around the entire device between the wall of the recipient vessel and the sealing device. The device may have small channels or guides for the suture.

Figure 23:
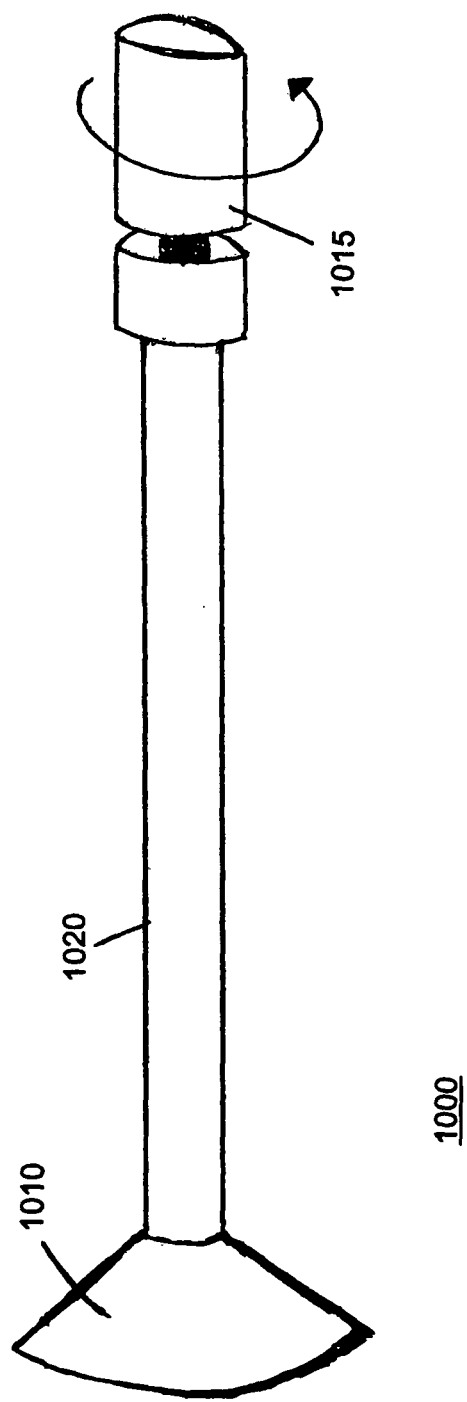
FIG. 23 is a schematic diagram of one embodiment of a vessel sealing device in accordance with the present invention.

FIG. 22 shows sealing member 1010 rolled up in a delivery configuration on shaft 1020. Following placement of sealing member 1010 within an opening in a vessel, sealing member 1010 may be "unrolled" thereby sealing the opening from fluid loss. FIG. 23 shows sealing member 1010 in an unrolled sealing configuration. Rotation of handle 1015 which is coupled to shaft 1020 and sealing member 1010 in one direction causes sealing member 1010 to unroll while rotation of handle 1015 in the opposite direction causes sealing member 1010 to roll up. Sealing member 1010 and shaft 1020 may be made of one or more suitable biocompatible or surgically acceptable materials as discussed above. Preferably, sealing member 1010 is made of a flexible material allowing it to be rolled and unrolled easily.

Figure 24:
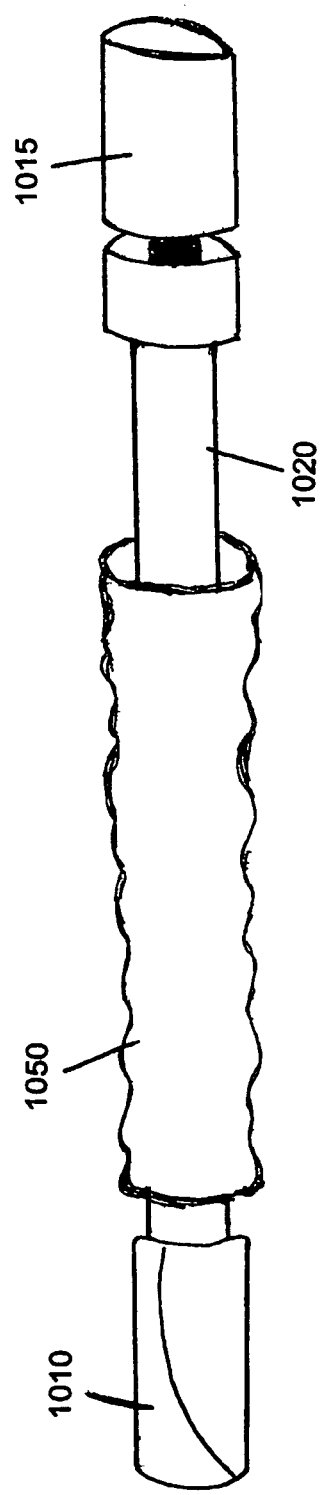
FIG. 24 is a schematic diagram of one embodiment of a vessel sealing device in accordance with the present invention.
Figure 25:
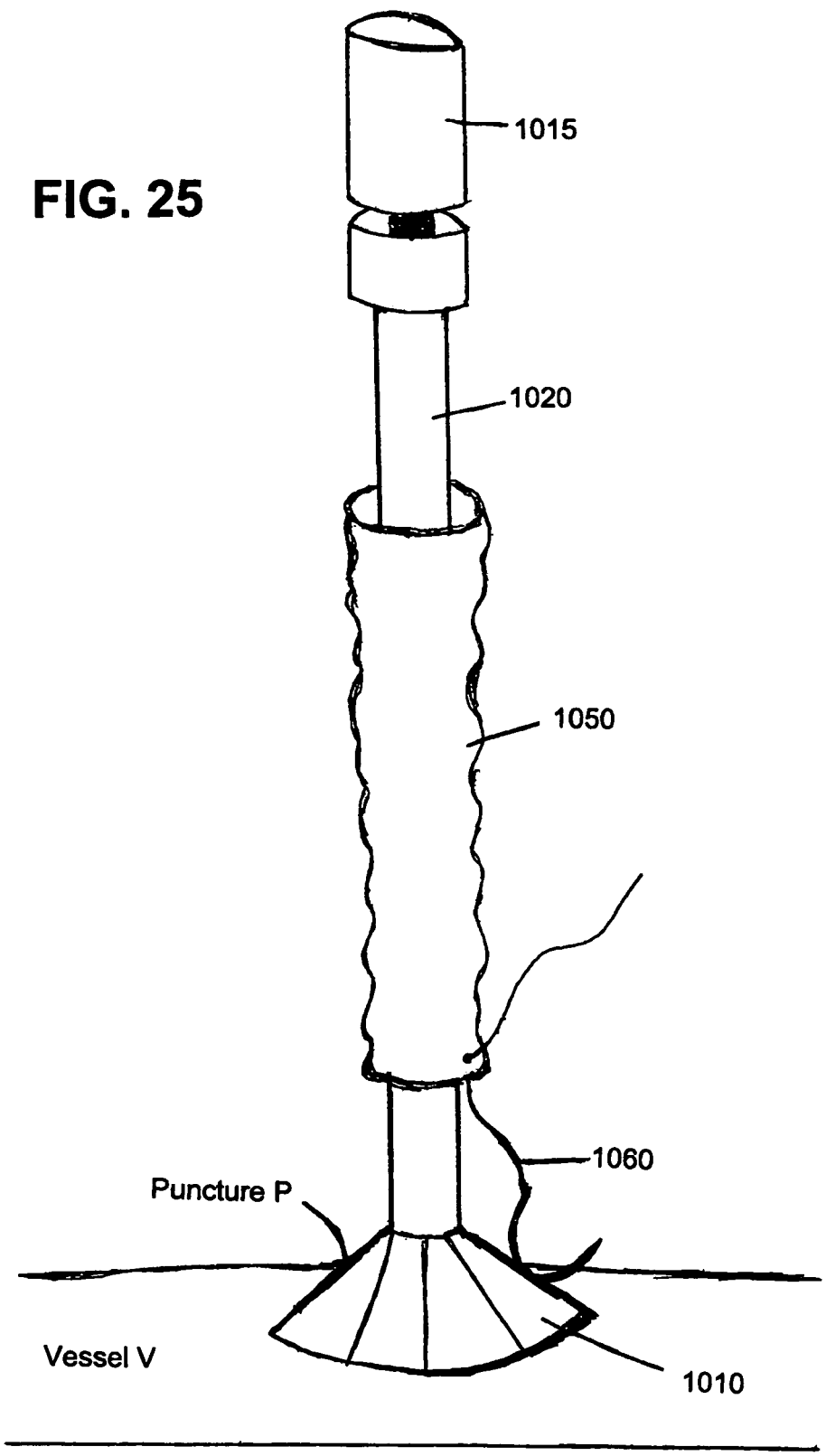
FIG. 25 is a schematic diagram of one embodiment of a vessel sealing device in accordance with the present invention.
Figure 26:
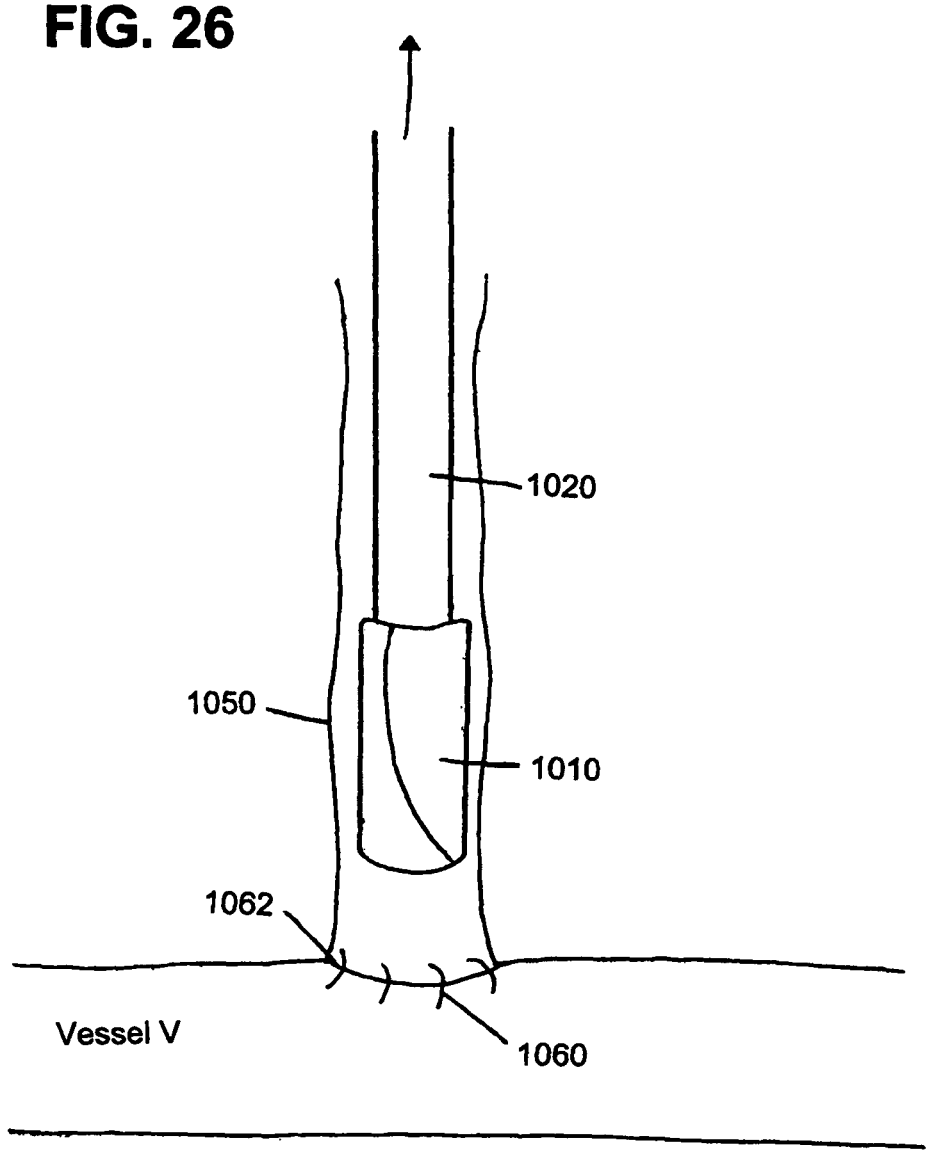
FIG. 26 is a schematic diagram of one embodiment of a vessel sealing device in accordance with the present invention.

FIG. 24 shows an embodiment of sealing device 1000 in a delivery configuration inserted through graft vessel 1050. Following the creation of an opening in vessel V, i.e., puncture P, sealing member 1010 is passed through puncture P and into vessel V. Sealing member 1010 is then deployed or unrolled into the appropriate configuration for sealing the opening in the vessel as shown in FIG. 25. After introduction into the vessel, the blood pressure will help sealingly engage sealing member 1010 with the inside of the wall of the vessel in the vicinity of the puncture P. To help engage sealing member 1010 with the inside wall of the vessel, an appropriate force, as mentioned above, may be exerted on sealing device 1000 in a direction away from the vessel, e.g., the surgeon may slightly pull back on the device to help more tightly engage sealing member 1010 with the edges of the opening in the vessel. Once in the proper position and configuration, the transmural pressure in the vessel will help keep the configured sealing member neatly apposed to the inner vessel wall, thereby sealing the opening, e.g., an arteriotomy or aortotomy. Once the opening is sealed, the graft vessel 1050 may be attached to the recipient vessel V, for example using one or more sutures 1060 as shown in FIG. 25. Once the anastomosis 1062 is completed as shown in FIG. 26, sealing member 1010 may be rolled back into its delivery configuration. Sealing member 1010 and shaft 1020 may then be removed through graft vessel 1050.

In one embodiment of the invention, seal member 1010 may comprise one or more ribs 1012. Ribs 1012 may be formed of suitable biocompatible material such as, for example, a biocompatible metal or polymer, which is impervious to blood. A biocompatible material would prompt little allergenic response and would be resistant to corrosion when placed within the patient's body. Alternatively, ribs 1012 may be made of material of suitable rigidity, which is coated with a biocompatible coating. Ribs 1012 may be formed of one or more materials that are more rigid than the sealing 1010, for example, ribs 1012 may be made of metal, e.g., stainless steel or nitinol, while seal 1010 may be made of flexible plastic, e.g., silicone rubber or polyurethane. Ribs 1012 may provide additional rigidity to seal 1010 following placement of seal 1010. As shown in FIG. 25, ribs 1012 may be formed in any suitable configuration on seal 1010, such as a plurality of ribs radiating outward on seal 1010 like the ribs of an umbrella.

Similar to earlier embodiments of the present invention, one or more components of sealing device 1000 may be made of one or more biocompatible materials. Further, one or more components of sealing device 1000 may be coated with one or more biological agents, e.g., an anti-coagulation agent such as heparin. The coatings may be hydrophilic or hydrophobic as desired.

In some embodiments of the invention, sutures and suture needles 1060 for completing the anastomosis may be guided into proper position by suture guides located on the surface of seal 1010 (not shown). In some embodiments of the invention, the material of seal 1010 may be compliant, such that the material of seal 1010 gives way to a suture needle, for example, thereby allowing the suture needle to be passed through graft vessel 1050, along the surface of seal 1010, and through vessel V, without puncturing seal 1010 and producing a leak. The material of seal 1010 may be designed to prevent punctures by suture needles or other sharp objects used in an anastomosis procedure.

Figure 27:
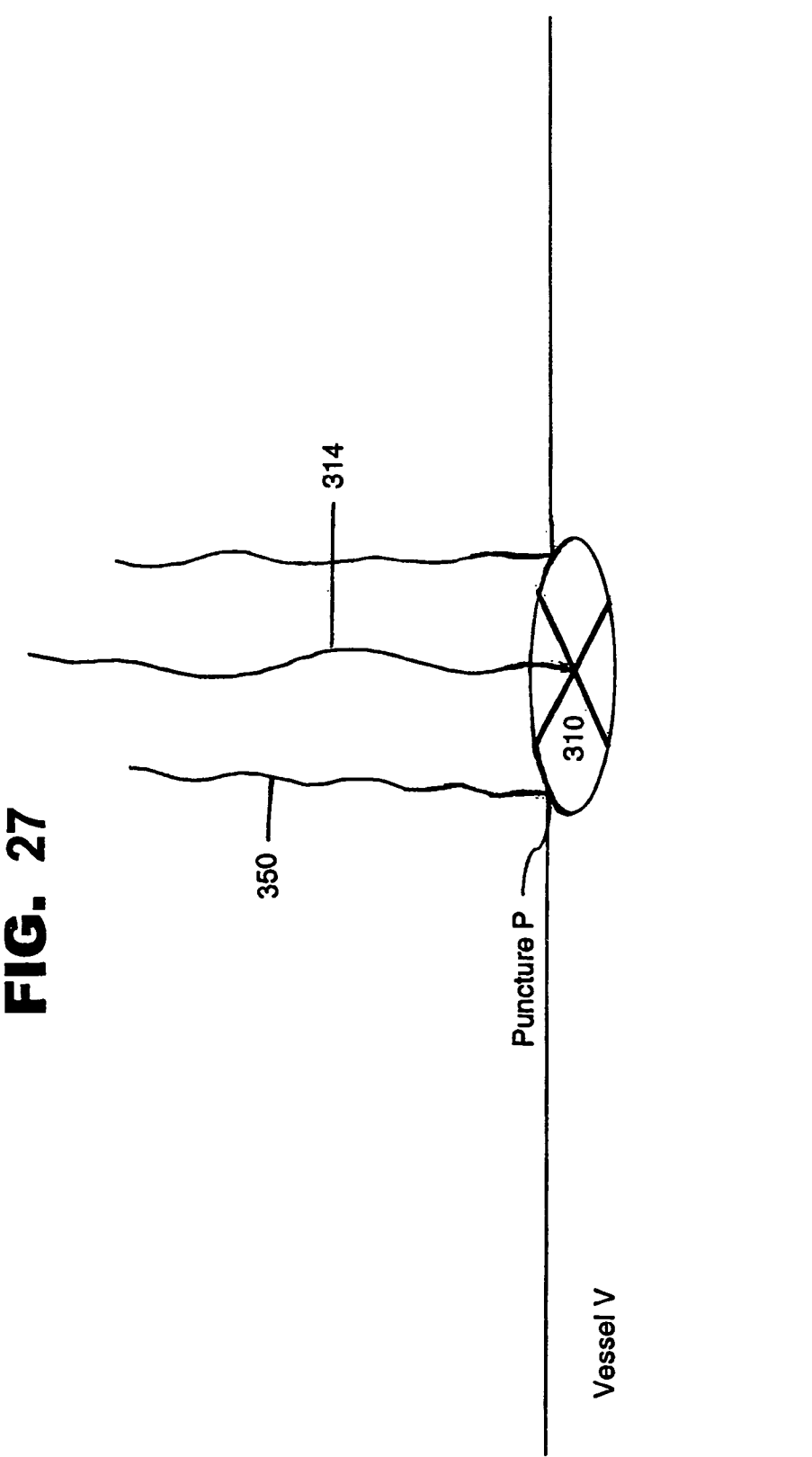
FIG. 27 is a schematic diagram of one embodiment of a vessel sealing device in accordance with the present invention.
Figure 28:
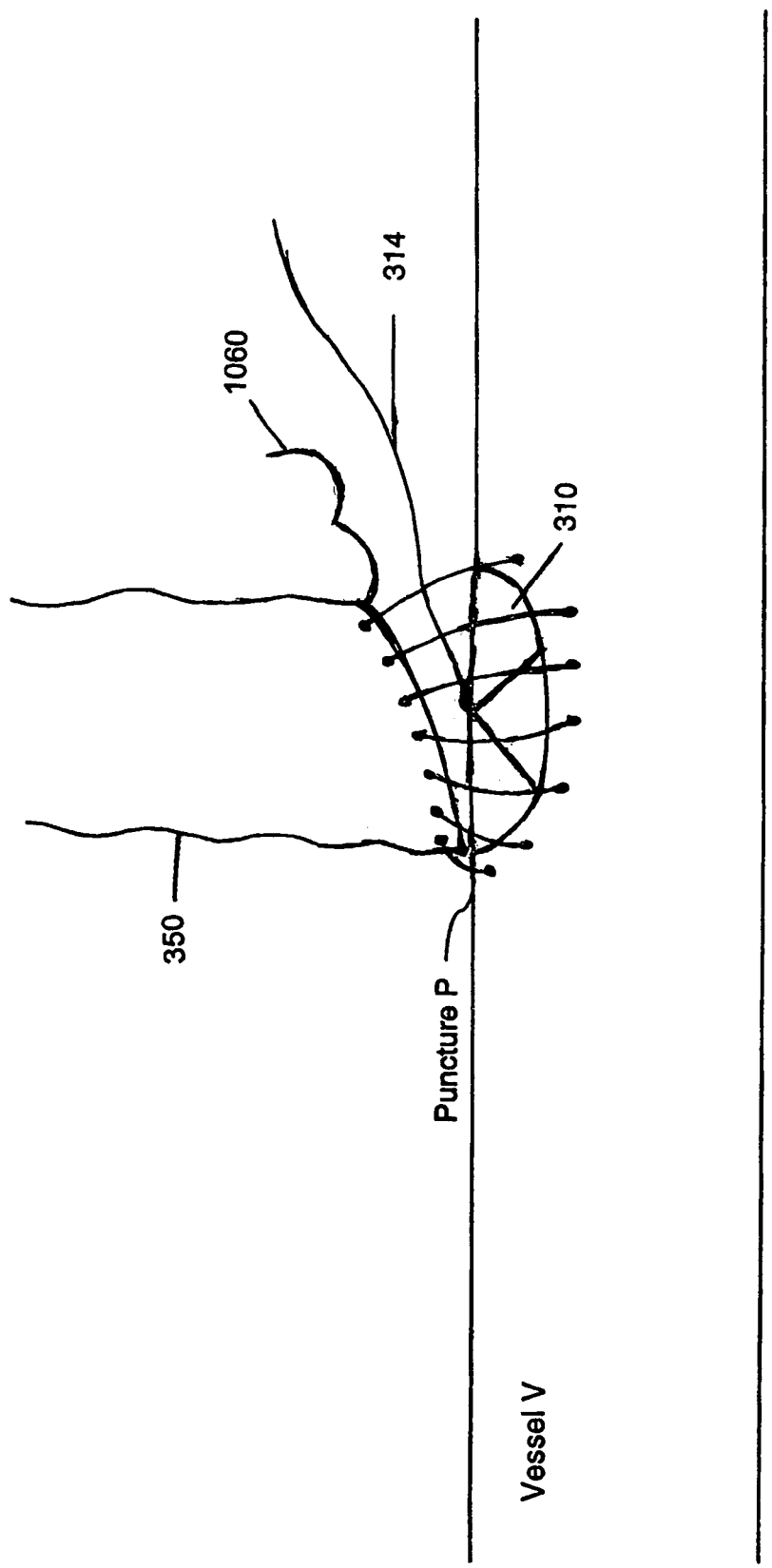
FIG. 28 is a schematic diagram of one embodiment of a vessel sealing device in accordance with the present invention.

As illustrated in various embodiments described above, the seal member of vessel sealing device may be delivered through an inner lumen of the tool body and placed adjacent an opening, e.g., incision or puncture, in a recipient vessel, thereby sealing the opening in the vessel. Following placement of the seal member, the tool body may be removed, leaving the seal member in place to seal the opening. The tool body may or may not comprise a cutting mechanism for creating an opening in the recipient vessel. The seal member may be attached to a tether or shaft. A graft vessel 350 may then be positioned adjacent the opening in the recipient vessel. The graft vessel may be positioned over the tether or shaft so as to position at least a portion of the tether or shaft within the lumen of the graft vessel (see FIG. 27). Upon completion of the anastomosis, the seal may be removed through the lumen of the graft vessel. Alternatively, the graft vessel may be positioned adjacent the opening in the recipient vessel so that the tether or shaft is positioned between the recipient vessel and the end of the graft vessel to be anastomosed to the recipient vessel (see FIG. 28). Prior to completion of the anastomosis, the seal may be removed from the opening between the graft vessel and the recipient vessel. Following removal of the seal, the anastomosis may be completed.

Figure 29:
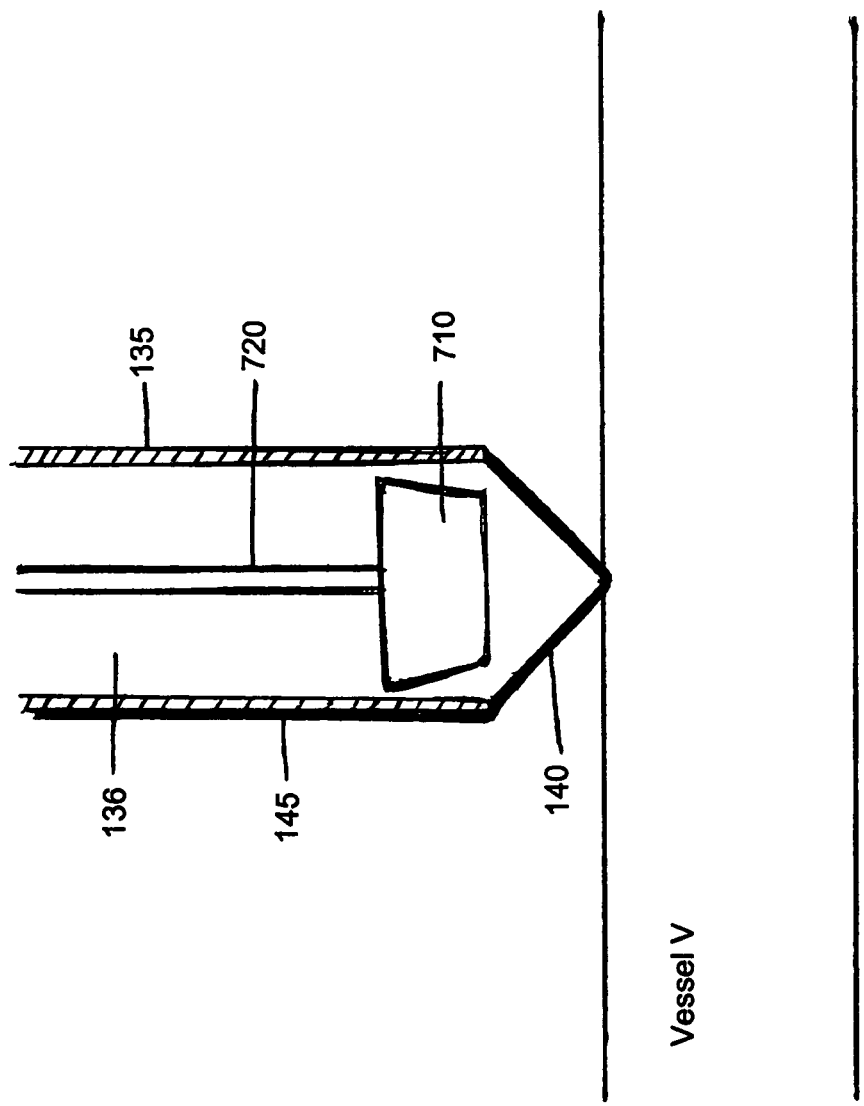
FIG. 29 is a schematic diagram of one embodiment of a vessel sealing device in accordance with the present invention.
Figure 30:
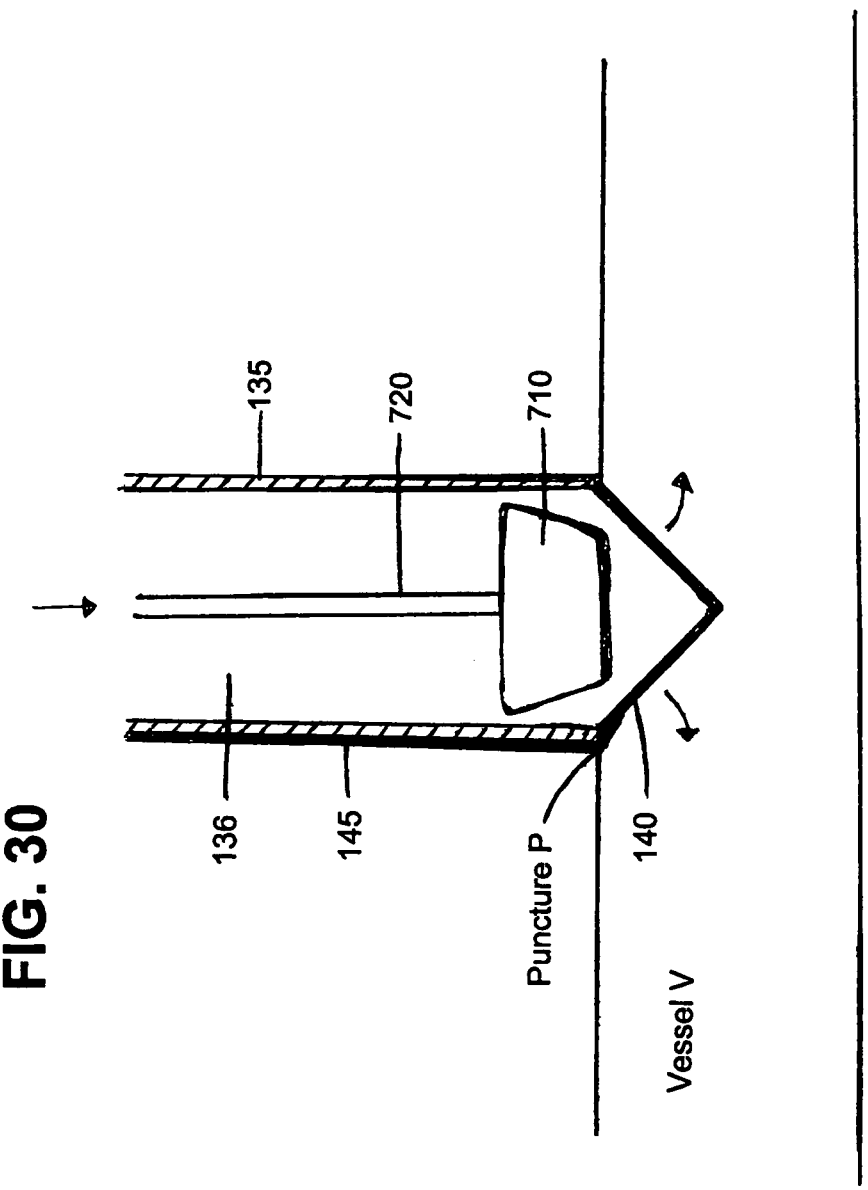
FIG. 30 is a schematic diagram of one embodiment of a vessel sealing device in accordance with the present invention.
Figure 31:
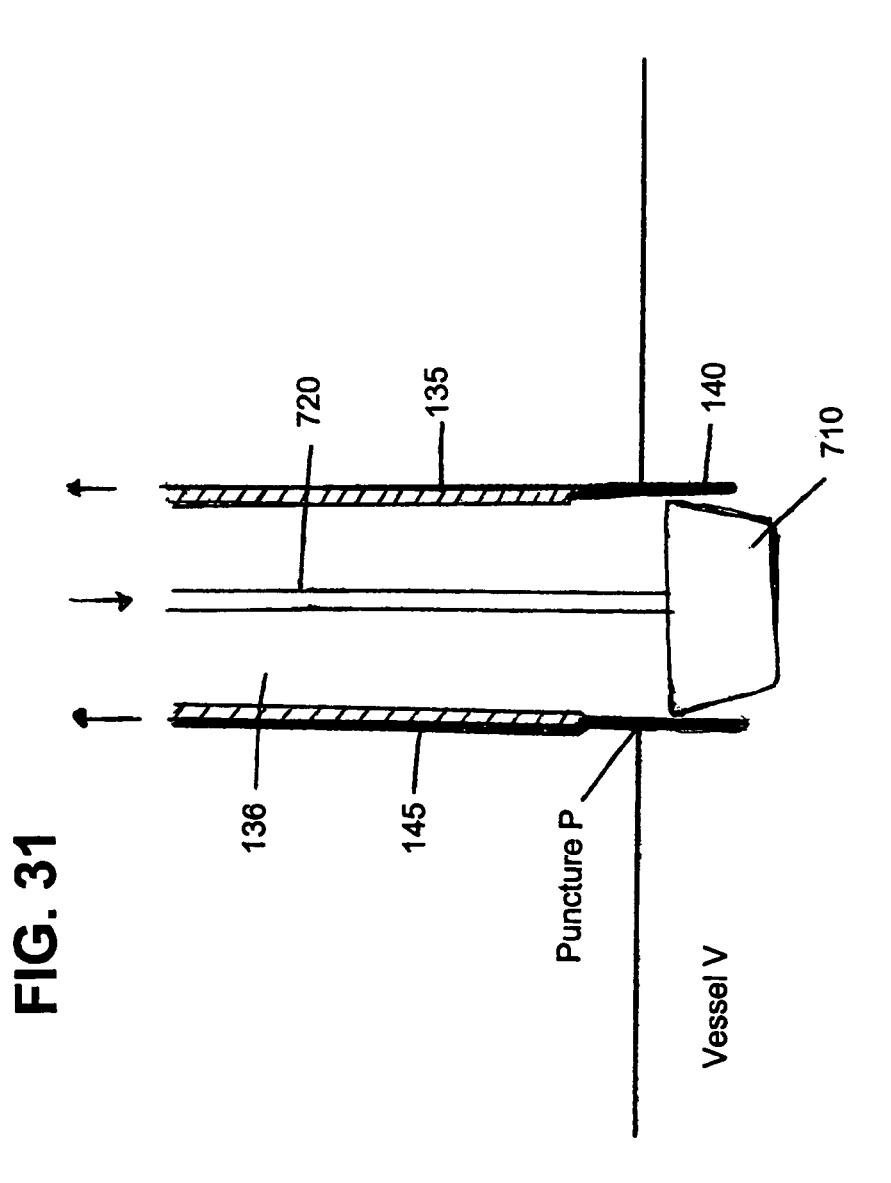
FIG. 31 is a schematic diagram of one embodiment of a vessel sealing device in accordance with the present invention.

FIG. 29 shows an alternative embodiment of a vessel sealing device in accordance with the present invention. In this embodiment, seal 710 and tether or shaft 720 are delivered through inner lumen 136 of tool body 135. Tool body 135 is coupled to cutting mechanism 140 which comprises one or more electrodes coupled to power conductor 145. Power conductor 145 conducts power to cutting electrodes 140. As described above, power conductor 145 may be connected to a power source by a power connector pin. Cutting electrode 140 is used to form an opening or incision in vessel V. While power is being provided to cutting electrode 140, cutting electrode 140 is advanced through the wall of vessel V (see FIG. 30), thereby creating an opening in vessel V. Seal 710 is advanced or pushed through lumen 136 of tool body 135, through cutting electrode 140 and into vessel V (see FIG. 31). Power may be provided to cutting electrode 140 at any time while seal 710 is advanced through lumen 136 of tool body 135, through cutting electrode 140 and into vessel V. Cutting mechanism 140 is coupled to the proximal end of tool body 135 so as to allow cutting mechanism 140 to change from a closed cutting configuration to an open delivery configuration. Therefore, as seal 710 is pushed into cutting mechanism 140, cutting mechanism 140 opens into a delivery configuration, thereby allowing seal 710 to move into vessel V. Once seal 710 is positioned in vessel V, cutting mechanism 140 may be removed from the opening in vessel V (see FIG. 32). Seal 710 may be left in place, thereby sealing the opening in vessel V, until a graft vessel is anastomosed to vessel V, as described above.

Figure 32:
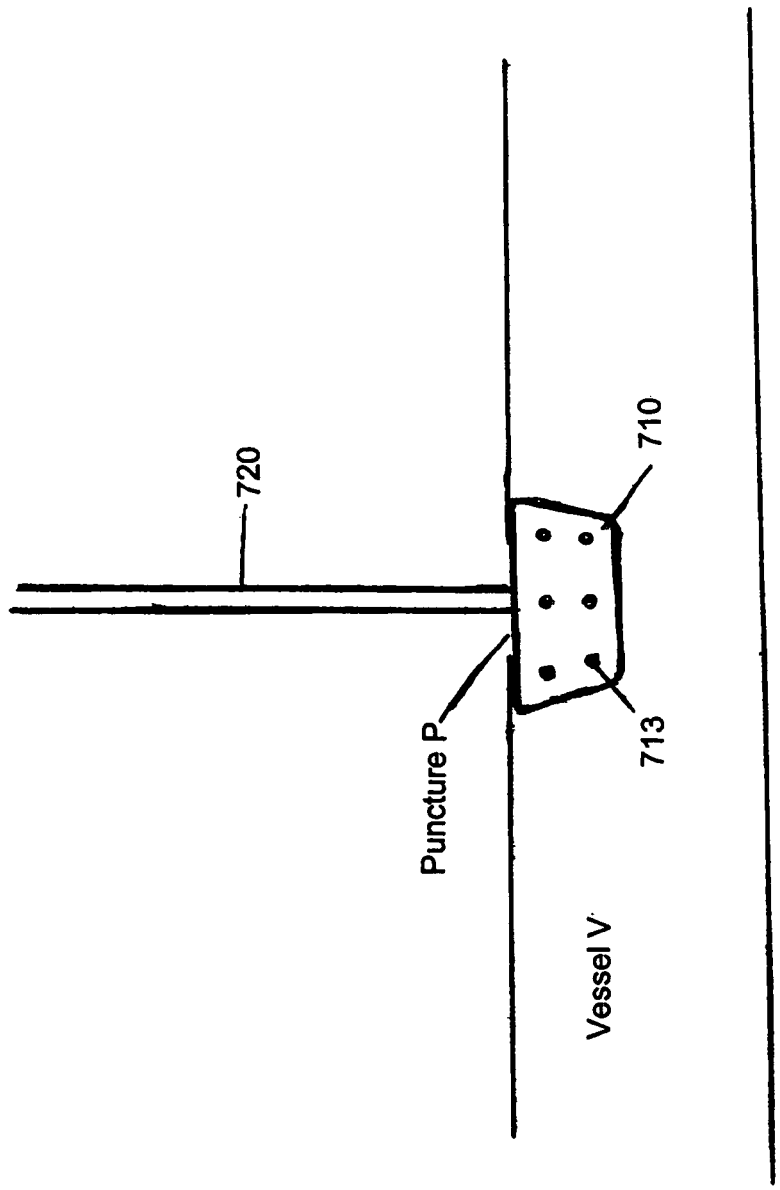
FIG. 32 is a schematic diagram of one embodiment of a vessel sealing device in accordance with the present invention.

FIG. 32 shows an alternative embodiment of seal member 710 in accordance with the present invention. In this embodiment, seal 710 may be used to deliver fluids and/or agents to the blood stream and/or vascular tissues. The fluids and/or agents, e.g., therapeutic agents, medical agents, biological agents, drugs and/or cells, may be delivered through an inner lumen of shaft 720 and out through one or more fluid openings 713. Fluid openings 713 may be fluidly coupled to one or more inner lumens of shaft 720. One or more biological glues, adhesives or sealants may be delivered, for example to help seal the anastomosis. RF energy may be delivered to the anastomosis to help close or seal the anastomosis.

Figure 33:
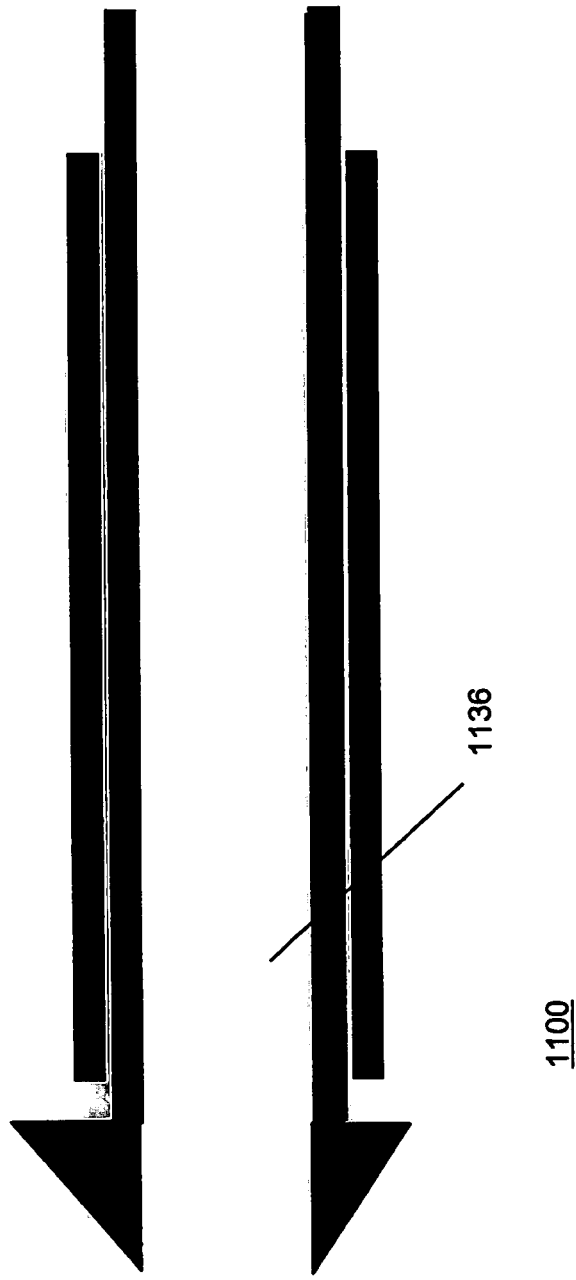
FIG. 33 is a schematic diagram of one embodiment of a vessel sealing device in accordance with the present invention.

FIG. 33 shows an alternative embodiment of a tissue punch 1100 that may be used in accordance with the present invention. In this embodiment, tissue punch, e.g., an aortic punch, 1100 having an internal lumen 1136 may be used to create a puncture or opening within a recipient vessel. The seal member of the vessel sealing device in accordance of the present invention may be delivered to the opening in the vessel through internal lumen 1136.

Figure 34:
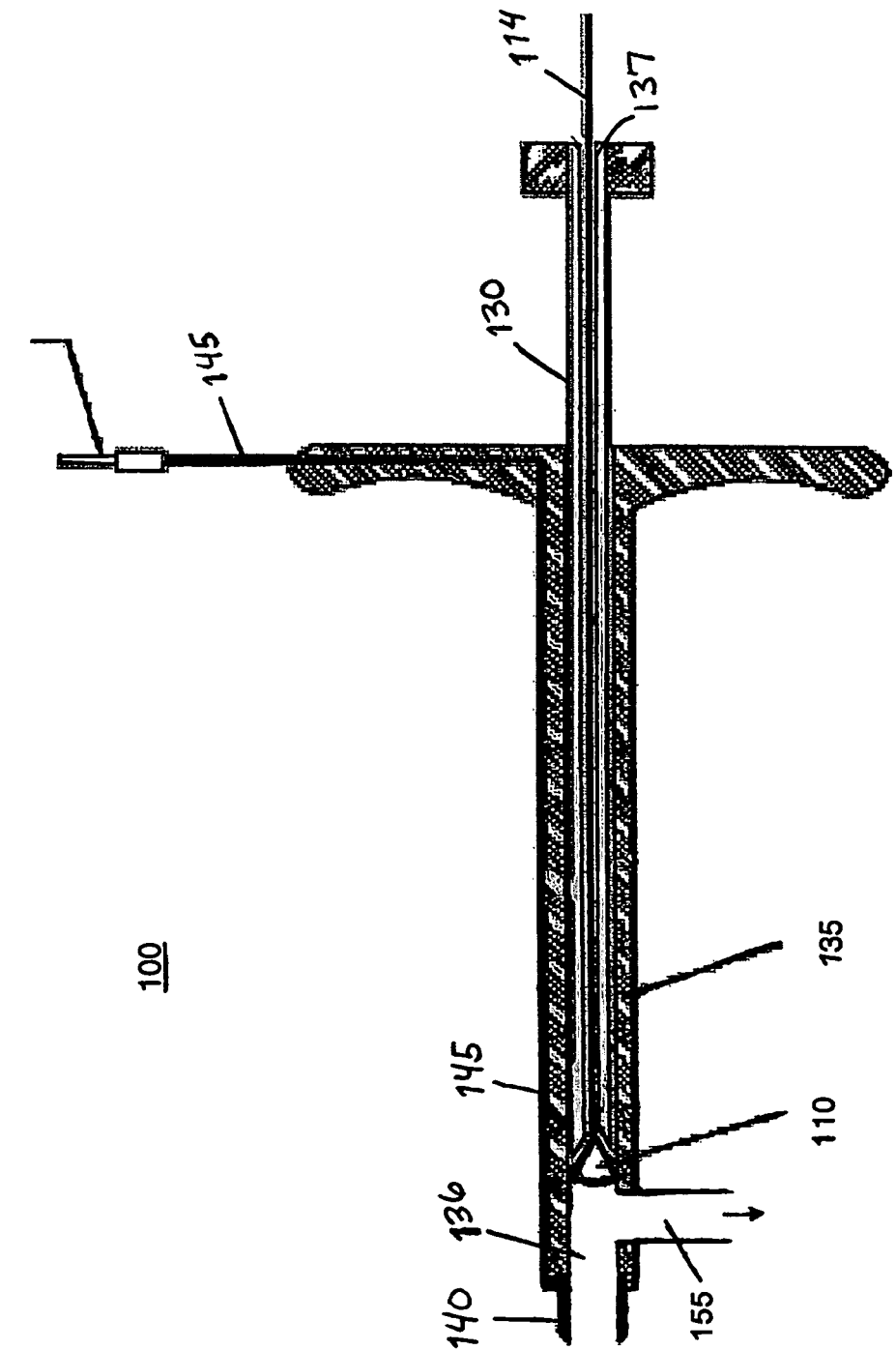
FIG. 34 is a schematic diagram of one embodiment of a vessel sealing device in accordance with the present invention.

FIG. 34 shows an alternative embodiment of vessel sealing device 100 that may be used in accordance with the present invention. Vessel sealing device 100 as shown in FIG. 34 includes a suction line or vacuum passage 155 coupled to inner lumen 136 of tool body 135. Suction line 155 may be coupled to a source of suction or vacuum. As used herein, the terms "vacuum" or "suction" refer to negative pressure relative to atmospheric or environmental air pressure in the operating room. Suction applied to the area of cutting mechanism 140 may be used to remove tissue debris or blood from the opening formed in the recipient vessel. For example, suction may be applied via suction line 155 so that a negative pressure is created in inner lumen 136. As cutting mechanism 140 cuts through tissue, thereby creating an opening in the vessel, any tissue debris created from the cutting procedure is drawn into inner lumen 136 and into suction line 155. Therefore, suction may be used to prevent tissue debris from entering the patient's blood stream, thereby preventing complications, e.g., clotting, downstream of the newly formed opening. Suction may also be used to position and/or hold vessel sealing device in position against or adjacent the recipient vessel.

Figure 35:
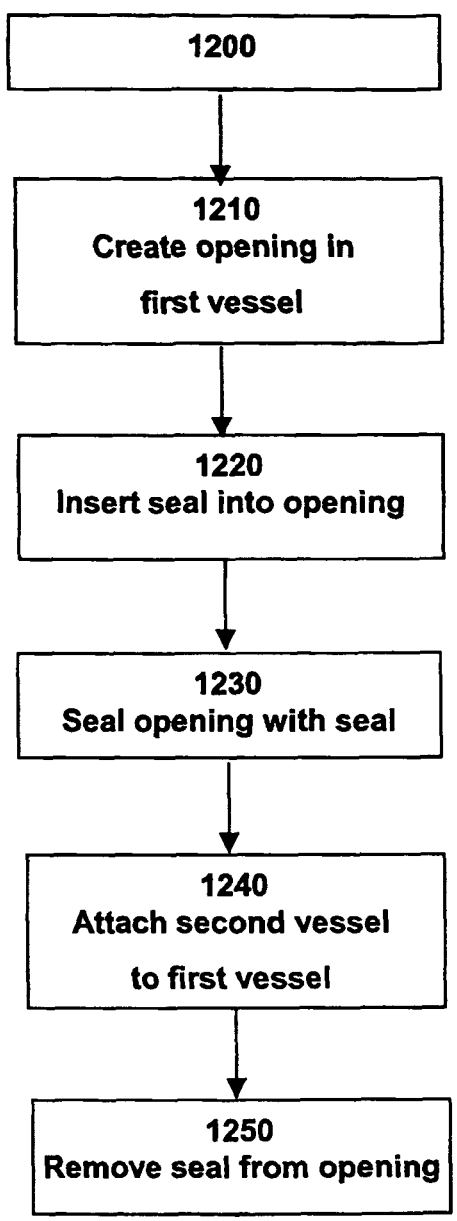
FIG. 35 is a flow diagram of one embodiment of a method for sealing a vessel in accordance with the present invention.

FIG. 35 shows one embodiment of a method for sealing a vessel in accordance with the present invention at 1200. As seen at block 1210, a puncture or opening is created within a first or recipient vessel using one or more of the cutting mechanisms described above. Alternatively, a conventional cutting means such as a scalpel or tissue punch, e.g., an aortic punch, may be used to create the opening. As seen at block 1220, a seal member is inserted into the opening. In one embodiment of the present invention, the seal member may be delivered into the opening through an inner lumen of a tool body as described above. Alternatively, the seal member may be delivered into the opening without use of a tool body. As seen at block 1230, the seal is deployed to an appropriate configuration to seal the opening. For example, the seal may be deployed to engage with the inside of the wall of the recipient vessel in the vicinity of the opening. Once in the proper place, the transmural pressure in the recipient vessel will keep the configured seal neatly apposed to the inner vessel wall, thereby sealing the opening, e.g., an arteriotomy or aortotomy. As seen at block 1240, a second or graft vessel is attached, e.g., via sutures, to the recipient vessel while the seal is in place. As seen at block 1250, once the anastomosis of the graft vessel to the recipient vessel has been completed, or substantially completed (e.g. all or most of the sutures are in place), the seal is removed. In one embodiment the seal is removed through the graft vessel. In an alternative embodiment, the seal is removed between the graft vessel and the recipient vessel.

For example, bypass grafting may be performed to provide adequate blood supply to an organ or tissue with impaired blood supply. In bypass grafting, the end of an extra vessel (the graft vessel) is connected, e.g., end-to-side or side-to-side, to the recipient vessel, e.g, an artery, downstream of the obstruction in the recipient vessel. To establish this connection, i.e. the distal anastomosis, the recipient vessel may first be opened via an incision or puncture. Next, the seal of the present invention is inserted through the opening and deployed thereby sealing the opening from blood loss. Next, the exit or distal end of the graft vessel is coupled, e.g., via suturing or other bonding method, to the recipient vessel. The seal may then be removed from the recipient vessel.

The inside of the graft vessel is generally sutured to the inside of the recipient vessel. The rationale of this precise anastomosis suturing is that the inner lining of the vessels (the endothelial lining) is anti-thrombogenic, whereas the outer layer is highly thrombogenic. Thrombosis at the transition of the graft vessel to the recipient vessel reduces the cross-sectional area of the lumen at the junction and hence jeopardizes the quality of the anastomosis. Narrowing or stenosis of the anastomosis limits the maximum blood flow through the bypass graft.

In a proximal anastomosis, the entrance (proximal end) of the bypass graft needs to be connected to a pressure source of oxygenated blood such as an artery or an aorta. If a natural artery can serve as bypass graft, like e.g. the internal mammary artery in coronary artery bypass grafting, only the distal anastomosis needs to be made. Sometimes, however, the internal mammary artery is used as free graft or the radial artery is used as arterial conduit and a proximal anastomosis has to be made. Venous bypass grafts always require a proximal anastomosis, because their transformation to an arterial conduit requires connection to a source of arterial blood.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. A method of constructing an anastomosis between a first vessel and a second vessel comprising: providing a device comprising an electrode for creating an opening in a vessel and a seal having a plurality of seal members for sealing the opening in the vessel; positioning the electrode adjacent a wall of the first vessel; applying sufficient energy to the electrode to form an opening in the first vessel; delivering the seal into the opening in the first vessel wherein the plurality of seal members are in a stacked first configuration; rotating a handle coupled to a shaft and to the seal members in a first direction to radially spread the plurality of seal members about an axis of the opening into a fanned-out second configuration to seal the opening; attaching the second vessel to the first vessel to form the anastomosis; rotating the handle in a second direction to arrange the plurality of seal members in the stacked first configuration; and removing the seal from the opening.

2. The method of claim 1 wherein the first configuration is a low-profile configuration.

3. The method of claim 1 wherein the second configuration is an expanded-profile configuration.

4. The method of claim 1 further comprising delivering one or more fluids to the first vessel while the seal is in a second configuration.

5. The method of claim 1 further comprising delivering one or more agents to the first vessel while the seal is in a second configuration.

6. A method of constructing an anastomosis between a first vessel and a second vessel comprising: providing a sealing assembly comprising a seal and a shaft wherein the seal includes a plurality of seal members; positioning the shaft so that at least a portion of the shaft is positioned within the second vessel; creating an opening in the first vessel; inserting the seal through the opening wherein the plurality of seal members are in a stacked first configuration; rotating a handle coupled to the shaft and to the seal members in a first direction to radially spread the plurality of seal members about an axis of the opening into a fanned-out second configuration to seal the opening; attaching the second vessel to the first vessel to form the anastomosis; rotating the handle in a second direction to arrange the plurality of seal members in the stacked first configuration; and removing the seal through the second vessel.

7. The method of claim 6 wherein the first configuration is a low-profile configuration.

8. The method of claim 6 wherein the second configuration is an expanded-profile configuration.

9. The method of claim 6 further comprising delivering one or more fluids to the first vessel while the seal is in a second configuration.

10. The method of claim 6 further comprising delivering one or more agents to the first vessel while the seal is in a second configuration.

* * * * *